US007414039B2

(12) United States Patent
Parsons

(10) Patent No.: US 7,414,039 B2
(45) Date of Patent: Aug. 19, 2008

(54) INTERSTITIAL THERAPY FOR IMMEDIATE SYMPTOM RELIEF AND CHRONIC THERAPY IN INTERSTITIAL CYSTITIS

(75) Inventor: C. Lowell Parsons, Henderson, NV (US)

(73) Assignee: The Regents of the University of California, Oakland, CA (US)

( * ) Notice: Subject to any disclaimer, the term of this patent is extended or adjusted under 35 U.S.C. 154(b) by 529 days.

(21) Appl. No.: 11/045,411

(22) Filed: Jan. 27, 2005

(65) Prior Publication Data

US 2005/0234013 A1 Oct. 20, 2005

Related U.S. Application Data

(60) Provisional application No. 60/540,186, filed on Jan. 28, 2004.

(51) Int. Cl.
*A61K 31/45* (2006.01)
*A61K 31/167* (2006.01)
*A61K 31/726* (2006.01)

(52) U.S. Cl. .......................... 514/57; 514/317; 514/626
(58) Field of Classification Search ........................ None
See application file for complete search history.

(56) References Cited

U.S. PATENT DOCUMENTS

| | | | |
|---|---|---|---|
| 4,460,360 A | 7/1984 | Finegold | |
| 4,879,282 A | 11/1989 | Saliba, Jr. | |
| 5,037,810 A | 8/1991 | Saliba, Jr. | |
| 5,104,856 A * | 4/1992 | Esko et al. | 514/26 |
| 5,137,528 A | 8/1992 | Crose | |
| 5,196,405 A | 3/1993 | Packman | |
| 5,374,624 A * | 12/1994 | Segel | 514/21 |
| 5,510,386 A | 4/1996 | Empfield et al. | |
| 5,749,845 A | 5/1998 | Hildebrand et al. | |
| 6,083,933 A | 7/2000 | Hahn | |
| 6,110,908 A * | 8/2000 | Guthery | 514/188 |
| 6,117,877 A | 9/2000 | Fogel | |
| 6,255,502 B1 | 7/2001 | Penkler et al. | |
| 6,648,863 B2 | 11/2003 | Reever | |
| 6,740,333 B2 | 5/2004 | Beckett et al. | |
| 2004/0142968 A1 | 7/2004 | Price et al. | |
| 2004/0161476 A1 | 8/2004 | Hahn et al. | |
| 2004/0209960 A1 | 10/2004 | Burgard et al. | |
| 2004/0248979 A1 | 12/2004 | Brettman et al. | |

FOREIGN PATENT DOCUMENTS

WO WO 02/41837 5/2002

OTHER PUBLICATIONS

Henry, R. et al "Absorption of alkalized intravesical lidocaine . . . " J. Urology (2001) vol. 165, pp. 1900-1903.*
Fukuda, T. et al "The effect of pH adjustment of 1% lidocaine . . . " J. Anesth. (1994) vol. 8, pp. 293-296.*
Buckley, M. et al "Characterization and immunohistochemical localization . . . " Arch. Biochem. Biophys. (1996) vol. 330, No. 1, pp. 163-173.*
Asklin, B. and J. Cassuto, "Intravesical Lidocaine in Several Interstitial Cystitis," *Scandinavian Journal of Urology and Nephrology*, 1989, 23:311-2. (Exhibit 50).
Higson, R. H. et al., "Intravesical Lignocaine and Detrusor Instability," *British Journal of Urology*, 1979, 51:500-3. (Exhibit 52).
Marrero, Ramon Perez et al., "Prolongation of Response to DMSO by Heparin Maintence," *Supplement to Urology*, 1993, 41:64-6. (Exhibit 53).
Parsons, C. Lowell, "Evidence-based strategies for recognizing and managing IC," *Contemporary Urology*, 2003, 1:270-7. (Exhibit 54).
Rovner, Eric et al., "Treatments Used in Women With Interstitial Cystitis: The Interstitial Cystitis Data Base (ICDB) Study Experience," *Urology*, 2000, 1:285-90. (Exhibit 55).
Sethia, K. K. and J. C. Smith, "The Effect of ph and Lignocaine on Detrusor Instability," *British Journal of Urology*, 1987, 60:516-8. (Exhibit 56).
Bernie, Jonathan E., et al, "The Intravesical Potassium Sensitivity Test and Urodynamics: Implications in a Large Cohort of Patients with Lower Urinary Tract Symptoms," *The Journal of Urology*, Jul. 2001, 166:158-61. (Exhibit 1).
Bjerklund Johansen, Truls E. and Wolfgang Weidner, "Understanding Chronic Pelvic Pain Syndrome," *Current Opinion in Urology*, 2002, 12:63-7. (Exhibit 2).
Forrest, John B. and Quang Vo, "Observations on the Presentation, Diagnosis and Treatment of Interstitial Cystitis in Men," *Urology*, 2001, 57(Suppl 6A):26-9. (Exhibit 3).
Hakenberg, Oliver W. and Manfred P. Wirth, "Chronic Pelvic Pain in Men," *Urol Int*, 2002, 68:138-43. (Exhibit 4).
Ho, Ngoc J., et al., "Natural History of Interstitial Cystitis in 274 Patients Receiving Sulfated Polysaccharide Therapy," *Urology*, 1999, 53:1133-9. (Exhibit 5).
Indudhara, R. et al., "Interstitial Cystitis in Males," *Urology*, Jun. 2001, 57 (Suppl 6A):120-1. (Exhibit 6).
Kusek, John W. and Leroy M. Nyberg, "The Epidemiology of Interstitial Cystitis: Is it Time to Expand Our Definition?" *Urology*, 2001, 57(Suppl 6A):95-9. (Exhibit 7).
Lilly, Joel D. and C. Lowell Parsons, "Bladder Surface Glycosaminoglycans is a Human Epithelial Permeability Barrier," *Surgery*, Dec. 1990, 171:493-6. (Exhibit 8).
Moldwin, Robert M., "Similarities Between Interstitial Cystitis and Male Chronic Pelvic Pain Syndrome," *Current Urology Reports*, 2002, 3:313-8. (Exhibit 9).
Nickel, J. Curtis, et al., "Pentosan Polysulfate Therapy for Chronic Nonbacterial Prostatis (Chronic Pelvic Pain Syndrome Category IIIA): A Prospective Multicenter Clinical Trial," *Urology*, 2000, 56:413-7. (Exhibit 10).
Novicki, Donald E., et al., "Interstitial Cystitis in Men," *Urology*, 1998, 52:621-4. (Exhibit 11).

(Continued)

*Primary Examiner*—Leigh C Maier
(74) *Attorney, Agent, or Firm*—Foley & Lardner LLP; Stephen E. Reiter

(57) ABSTRACT

The present invention relates to a disorder of the lower urinary tract, and in particular, reducing the symptoms (including treatment) of interstitial cystitis in vivo. In a preferred embodiment, the present invention relates to treatment formulations and methods for reducing interstitial cystitis in patients.

22 Claims, 10 Drawing Sheets

OTHER PUBLICATIONS

Parsons, C. L. et al., "Treatment of Interstitial Cystitis with Intravesical Heparin," *British Journal of Urology*, 1994, 73:504-7. (Exhibit 12).

Parsons, C. Lowell, "Epithelial Coating Techniques in the Treatment of Interstitial Cystitis," *Urology*, 1997, 49(Suppl 5A):100-4. (Exhibit 13).

Parson, C. Lowell, "Intravesical Potassium Sensitivity in Patients with Interstitial Cystitis and Urethral Syndrome," *Urology*, 2001, 57:428-33. (Exhibit 14).

Parsons, C. Lowell, "Prostatitis, Interstitial Cystitis, Chronic Pelvic Pain, And Urethral Syndrome Share a Common Pathophysiology: Lower Urinary Dysfunctional Epithelium and Potassium Recycling," *Urology*, 2003, 62:976-82. (Exhibit 15).

Parsons, C. Lowell, "Successful Downregulation of Bladder Sensory Nerves with Combination of Heparin and Alkalinized Lidocaine in Patients with Interstitial Cystitis," *Urology*, 2005, 65:45-8. (Exhibit 16).

Parsons, C. Lowell, "The Therapeutic Role of Sulfated Polysaccharides in the Urinary Bladder," *Urologic Clinics of North America*, Feb. 1994, 21(1):93-100. (Exhibit 17).

Parsons, C. Lowell and Michael Albo, "Intravesical Postassium Sensitivity in Patients with Prostatitis," *The Journal of Urology*, Sep. 2002, 168:1054-57. (Exhibit 18).

Parsons, C. Lowell and Vasiliki Tatsis, "Prevalence of Insterstitial Cystitis in Young Women," *Urology*, 2004, 64:866-70. (Exhibit 19).

Parsons, C. Lowell, et al., "Abnormal Urinary Potassium Metabolism in Patients with Interstitial Cystitis," *The Journal of Urology*, Apr. 2005, 173: 1182-5. (Exhibit 20).

Parsons, C. Lowell, et al., "A Quantitatively Controlled Method to Study Prospectively Insterstitial Cystitis and Demonstrate the Efficacy of Pentosanpolysulfate," *The Journal of Urology*, Sep. 1993, 150:845-8. (Exhibit 21).

Parsons, C. Lowell, et al., "Bladder-Surface Glycosaminoglycans: An Efficient Mechanism of Environmental Adaptation," *Science*, May 9, 1980, 209(4444):605-7. (Exhibit 22).

Parsons, C. Lowell, et al., "Bladder-Surface Glycosaminoglycans: An Epithelial Permeability Barrier," *The Journal of Urology*, Jan. 1990, 143:139-142. (Exhibit 23).

Parsons, C. Lowell, et al., "Effect of Pentosan Polysulfated Therapy On Intravesical Potassium Sensitivity," *Urology*, 2002, 59:329-33. (Exhibit 24).

Parsons, C. Lowell, et al., "Epithelial Dysfunction in Nonbacterial Cystitis (Insterstitial Cystitis)," *The Journal of Urology*, Apr. 1991, 145:732-5. (Exhibit 25).

Parsons, C. Lowell, et al., "Increased Prevalence of Interstitial Cystitis: Previously Unrecognized Urologic and Gynecologic Cases Identified Using A New Symptom Questionnaire and Intravesical Potassium Sensitivity," *Urology*, 2002, 60:573-8. (Exhibit 26).

Parsons, C. Lowell, et al., "Quantifying Symptoms in Men with Interstitial Cystitis/Prostatis, and its Correlation with Potassium-Sensitivity Testing," *BJU International*, 2005, 95:86-90. (Exhibit 27).

Parsons, C. Lowell, et al, "The Prevalence of Interstitial Cystitis in Gynecologic Patients with Pelvic Pain, As Detected by Intravesical Potassium Sensitivity," *American Journal of Obstetrics and Gynecology*, Nov. 2002, 187(5):1-10. (Exhibit 28).

Parsons, C. Lowell, et al., "The Role of Urinary Potassium in the Pathogenesis and Diagnosis of Interstitial Cystitis," *The Journal of Urology*, Jun. 1998, 159(6):1862-7. (Exhibit 29).

Saada, Janak, et al., "Computed Tomography and Magnetic Resonance Imaging in the Management of Prostate Cancer," Textbook of Prostatitis, pp. 169-176. (Exhibit 30), 1999.

Waxman, Jeffrey A., et al., "Cytoscopic Findings Consistent with Interstitial Cystitis in Normal Women Undergoing Tubal Ligation," *The Journal of Urology*, Nov. 1998, 160(5):1663-7. (Exhibit 31).

Wesselmann, Ursula, "Neurogenic Inflammation and Chronic Pelvic Pain," *World J Urol*, 2001, 19:180-5. (Exhibit 32).

* cited by examiner

Please circle the answer that best describes how you feel for each question.

| | | 0 | 1 | 2 | 3 | 4 | SYMPTOM SCORE | BOTHER SCORE |
|---|---|---|---|---|---|---|---|---|
| 1 | How many times do you go to the bathroom during the day? | 3-6 | 7-10 | 11-14 | 15-19 | 20+ | | |
| 2 | a. How many times do you go to the bathroom at night? | 0 | 1 | 2 | 3 | 4+ | | |
| | b. If you get up at night to go to the bathroom, does it bother you? | Never | Occasionally | Usually | Always | | | |
| 3 | Are you currently sexually active. YES ___ NO ___ | | | | | | | |
| 4 | a. IF YOU ARE SEXUALLY ACTIVE, do you now or have you ever had pain or symptoms during or after sexual intercourse? | Never | Occasionally | Usually | Always | | | |
| | b. If you have pain, does it make you avoid sexual intercourse? | Never | Occasionally | Usually | Always | | | |
| 5 | Do you have pain associated with your bladder or in your pelvis (vagina, labia, lower abdomen, urethra, perineum, testes or scrotum)? | Never | Occasionally | Usually | Always | | | |
| 6 | Do you still have urgency after you go to the bathroom? | Never | Occasionally | Usually | Always | | | |
| 7 | a. If you have pain, is it usually | | Mild | Moderate | Severe | | | |
| | b. Does your pain bother you? | Never | Occasionally | Usually | Always | | | |
| 8 | a. If you have urgency, is it usually | | Mild | Moderate | Severe | | | |
| | b. Does your urgency bother you? | Never | Occasionally | Usually | Always | | | |

| | |
|---|---|
| SYMPTOM SCORE (1, 2a, 4a, 5, 6, 7a, 8a) | |
| BOTHER SCORE (2b, 4b, 7b, 8b) | |
| TOTAL SCORE (Symptom Score + Bother Score) = | |

Figure 1

How IC presents itself in women and men

*Pelvic pain:*

- Can be felt as dysuria, pain in the suprapubic area, lower abdomen, lower back, medial thighs, inguinal area, urethra, vagina or vulva in women, scrotum or testes in men

- Can occur in multiple locations in any combination

- Includes pain with sexual intercourse, present in many male and female IC patients

- May be the IC patient's only symptom (some have no urgency/frequency)

*Urinary urgency/frequency:*

- Tends to develop gradually

- May be present but the patient may not recognize it as abnormal

- May be the IC patient's only symptom (some have no pain)

- May occur in precipitous flares in as little as one hour

Figure 3

Factors that can affect the severity of an IC patient's symptoms on a given day

- Duration of disease - has the patient had continuous symptoms for 6 months or more?

- Tissues affected - bladder, urethra, and/or prostate

- Treatment(s) received

- Level of recent sexual activity - symptoms often flare during or within 24-48 hours after intercourse in females and males

- Menstrual cycle - symptoms tend to flare before onset of menses

- Seasonal allergies

Figure 4

PUF Score as a Predictor of PST Result*

| PUF Score | Likelihood of Positive PST |
|---|---|
| 10-14 | 75% |
| 15-19 | 79% |
| 20+ | 94% |

*Source of data: Parsons *et al.* Urology. 60:573-578 (2002)

Figure 5

Three-part treatment regimen for IC

*Restoring epithelial function:*

- Pentosan polysulfate (oral) 300-900 mg/day

- Heparin (intravesical) 40,000 IU in 8 cc 1% lidocaine and 3 ml of sodium bicarbonate once to twice a day

*Reversing neural activation:*

- Preferred: Amitriptylene (Elavil) 25 mg/day at bedtime

- Can increase to 50 mg/day after 4-8 weeks

- Alternative: selective serotonin reuptake inhibitor

*Controlling allergies:*

- Hydroxyzine 25 mg daily in the evening

- Increase to 50-100 mg daily during allergy seasons as needed

Figure 6

CME Educational Objectives

*Upon completion of this CME review article, the participant should be able to:*

- List the clinical signs and symptoms of interstitial cystitis

- Relate several factors that complicate the process of diagnosing IC

- Compare the effectiveness of cystoscopy versus the Potassium Sensitivity Test in establishing a diagnosis of IC

- Describe the rationale and the procedure for the Potassium Sensitivity Test

- Outline a heparinoid-based program of medical therapy for an IC patient who has seasonal allergies

- Describe how and when the success of this therapy should be assessed

Figure 7

Objectives for the Clinician

*Diagnosis*

- Use the PUF Scale to screen patients for IC symptoms

- Suspect IC in a woman or man who has urinary urgency and/or pelvic pain in the absence of any other identifiable cause

- Bear in mind that a patient may feel IC pain in one or more places in the front or back of the pelvic area, from the navel to the thighs, in any combination

- Rely on the Potassium Sensitivity Test to confirm the diagnosis of IC

*Treatment*

- Make heparinoid therapy the cornerstone of your IC treatment plan

- Use medical therapies aimed at reversing neural activation and controlling allergies as appropriate

- Try PPS therapy for at least a year before judging its effectiveness

- Never withhold IC treatment from a patient who has signs and symptoms of IC but tests negative for intravesical potassium sensitivity

Figure 8

Patient Overall Rating of Improvement of Symptoms
(PORIS)

Please check the category that BEST describes your condition TODAY in COMPARISON to your condition BEFORE you started therapy.

1. Please check the category that best describes the OVERALL CHANGE in PAIN associated with your bladder since the start of
   therapy. (Check one)

[ ] Worse
   [ ] No better (0% improvement)
   [ ] Slightly improved (25% improvement)
   [ ] Moderately improved (50% improvement)
   [ ] Greatly improved (75% improvement)
   [ ] Symptoms gone (100% improvement)

2. Please check the category below that best describes the OVERALL CHANGE in URGENCY or pressure to urinate associated with your bladder since the start of therapy. (Check one)

[ ] Worse
   [ ] No better (0% improvement)
   [ ] Slightly improved (25% improvement)
   [ ] Moderately improved (50% improvement)
   [ ] Greatly improved (75% improvement)
   [ ] Symptoms gone (100% improvement)

Figure 9

INTERSTITIAL THERAPY FOR IMMEDIATE SYMPTOM RELIEF AND CHRONIC THERAPY IN INTERSTITIAL CYSTITIS

This application is based on U.S. Provisional Application Ser. No. 60/540,186 filed on Jan. 28, 2004, the contents of which are hereby incorporated by reference, in their entirety, into this application, and from which priority is hereby claimed.

Throughout this application various publications are referenced. The disclosures of these publications in their entireties are hereby incorporated by reference into this application in order to more fully describe the state of the art to which the invention pertains.

FIELD OF THE INVENTION

The present invention relates to a disorder of the lower urinary tract, and in particular, reducing the symptoms (including treatment) of interstitial cystitis in vivo. In a preferred embodiment, the present invention relates to, treatment formulations and methods for reducing interstitial cystitis in patients.

BACKGROUND OF THE INVENTION

Interstitial cystitis (IC) is a chronic progressive disorder of the lower urinary tract that causes urinary urgency and frequency and/or pelvic pain. For many years, urologists regarded IC as a rare disease for which they had no broadly effective treatment. In fact, the condition is quite common. In 1999, prevalence in the United States was estimated at 750,000 cases (Curhan, et al. J Urol 161(2):549-552 (1999)). However the true prevalence of IC is estimated to be at least 1-2 million patients who are suffering from severe chronic pelvic pain.

Treatments with dimethylsulfoxide (DMSO), approved for IC in 1977 on the basis of data from uncontrolled trials, can be useful with weekly intravesical instillations for 6 to 8 weeks then every two weeks for 3-12 months for maintenance. However DMSO therapy results in benefit for approximately 50% of IC patients treated and the treatment takes a long time to reduce symptoms. Furthermore, this therapy causes pain that is unrelieved by local anesthetics by themselves due to their lack of absorption into the bladder wall. Narcotics are given for immediate relief of symptoms however they are only minimally effective. Some patients benefit from formal 8- to 12-week, one-on-one course of behavior modification. Patients are also advised to avoid potassium-rich foods, particularly citrus fruits, tomatoes, chocolate, and coffee.

Therefore, treatments that would both benefit a larger portion of the patient population, provide immediate relief of symptoms without causing additional pain, without requiring extensive alterations in diet, and further provide reversal of the disease process over time are necessary. The present invention meets that challenge by providing compositions, detection methods and novel IC management treatment methods with the benefits described herein.

SUMMARY OF THE INVENTION

The present invention relates to a disorder of the lower urinary tract, and in particular, reducing the symptoms (including treatment) of interstitial cystitis in vivo. In a preferred embodiment, the present invention relates to treatment formulations and methods for reducing interstitial cystitis in patients.

In some embodiments, the present invention provides treatment formulations for reducing one or more of the following urinary frequency, urgency, and/or pelvic pain. In one embodiment, the present invention contemplates treating patients with interstitial cystitis (IC). While it is not intended that the present invention be limited to any particular form of IC, it is believed that the majority of IC patients would benefit from this invention. In further embodiments, the present invention contemplates treating patients with any one or more of the following: urinary frequency, urgency, and/or pelvic pain.

In one embodiment, the present invention contemplates a composition comprising: a) a heparinoid, b) a local anesthetic, and c) a buffering compound. In one embodiment, the composition is in a solid state. In one embodiment, the composition is in solution. In one embodiment, the composition is in solution, wherein said solution has a pH of at least 7. In one embodiment, the composition is in solution, wherein said solution has a pH of at least 8. In one embodiment, the composition is in solution, wherein said solution has a pH from 7 to 12. Accordingly in some embodiments, the pH of said solution is at 7.0, 8.0, 9.0, 10.0, 11.0, 12.0 (or any pH value between 7 and 12). The pH of the composition is chosen to be near to the pKa of the local anesthetic.

In one embodiment, said composition comprises a heparinoid. Indeed a variety of heparins and related heparinoid compounds are contemplated, including, but not limited to one or more of the following: heparin sodium, pentosan polysulfate sodium, heparan sulfate, hyaluronic acid, chondroitin sulfate, glycosaminoglycans and the like. In one embodiment, said composition comprises at least 100 units of heparin per unit dose. In one embodiment, said composition comprises at least 10,000 units of heparin per unit dose. In one embodiment, said composition comprises from 10,000 to 40,000 units of heparin per unit dose. Accordingly in some embodiments, said composition comprises 100 units, 10,000 units, 40,000 units (or any amount between 100 units and 40,000 units) of heparin per unit dose. The present invention is not limited to any particular heparin. In one embodiment, said composition comprises from 100 mg to 600 mg pentosan polysulfate sodium per unit dose. Accordingly in some embodiments, said composition comprises 100 mg, 200 mg, 300 mg, 400 mg, 500 mg, 600 mg (or any amount between 100 mg and 600 mg) pentosan polysulfate sodium per unit dose. The quantities for other heparinoids can be chosen according to their activity by one of ordinary skill in the art.

The present invention is not limited to any particular local anesthetic or formulation. In some embodiments, the local anesthetic comprises lidocaine. Typically, the local anesthetic is selected from the group consisting of benzocaine, lidocaine, tetracaine, bupivacaine, cocaine, etidocaine, flecainide, mepivacaine, pramoxine, prilocalne, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Preferably, the local anesthetic is selected from the group consisting of lidocaine, bupivicaine, benzocaine, tetracaine, etidocaine, flecainide, prilocalne, and dibucaine. More preferably, the local anesthetic is lidocaine.

In one embodiment, said buffering compound comprises sodium bicarbonate. The present invention is not limited to any particular buffering compound. Typically, the buffer is selected from the group consisting of bicarbonate buffer, THAM or Tris (Tris(hydroxymethyl)aminomethane) buffer, MOPS buffer (3-(N-morpholino)propanesulfonic acid), HEPES (N-(2-hydroxyethyl)piperazine-N'-(2-ethanesulfonic acid) buffer, ACES (2-[(2-amino-2-oxoethyl)amino] ethanoesulfonic acid) buffer, ADA (N-(2-acetamido)2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid) buffer, CHES (2-(N-cyclohexylamino) ethanesulfonic acid) buffer, DIPSO (3-[N,N-bis(2-hydroxyethyl)amino]-2-hydroxy-propanesulfonic acid) buffer, HEPPS(N-(2-hydroxyethylpiperazine)-N-(3-propanesulfonic acid), buffer, HEPPSO(N-(2-hydroxyethyl)piperazine-N-(2-hydroxypropanesulfonic acid) buffer, MES (2-(N-morpholino)ethanesulfonic acid) buffer, triethanolamine buffer, imidazole buffer, glycine buffer, ethanolamine buffer, phosphate buffer, MOPSO (3-(N-morpholino)-2-hydroxypropanesulfonic acid) buffer, PIPES (piperazine-N,N-bis(2-ethanesulfonic acid) buffer, POPSO (piperazine-N,N'-bis(2-hydroxypropaneulfonic acid) buffer, TAPS(N-tris (hydroxymethyl)methyl-3-aminopropanesulfonic acid) buffer; TAPSO (3-[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, and 2-amino-2-methyl-1-propanol buffer. Preferably, the buffer is sodium bicarbonate buffer, Tris buffer, phosphate buffer, MOPS buffer, or HEPES buffer.

In one embodiment, the present invention contemplates methods for reducing one or more of the following urinary frequency, urgency, and/or pelvic pain. In some embodiments, one or more of urinary frequency, urgency, and/or pelvic pain relates to interstitial cystitis (IC). In some embodiments, the present invention contemplates methods for reducing interstitial cystitis in patients. In some embodiments, a method for reducing symptoms of interstitial cystitis comprises administering any one of the above compositions to a subject. In some embodiments, a method for reducing symptoms of interstitial cystitis comprises administering any one or more of an oral heparinoid in combination with any one of the above compositions to a subject. In some embodiments, said subject is human. In some embodiments, said administering comprises intravesical administration. In some embodiments, said administering comprises one or more of oral and intravesical administration. In some embodiments, said administering further comprises a composition comprising 100 mg/day to 300 mg/day pentosan polysulfate sodium. In some embodiments, said administering further comprises a composition comprising 100 mg/day to 600 mg/day pentosan polysulfate sodium.

BRIEF DESCRIPTION OF THE DRAWINGS

FIG. 1 shows an exemplary embodiment of a PELVIC PAIN and URGENCY/FREQUENCY PATIENT SYMPTOM (PUF) SCALE.

FIG. 3 (Table 1) shows an exemplary embodiment of how IC presents itself in women and men.

FIG. 4 (Table 2) shows an exemplary embodiment of factors that can affect the severity of an IC patient's symptoms on a given day.

FIG. 5 (Table 3) shows an exemplary embodiment of PUF Score as a Predictor of PST Result.

FIG. 6 (Table 4) shows an exemplary embodiment of a three-part treatment regimen for IC.

FIG. 7 (Table 5) shows an exemplary embodiment of CME Educational Objectives.

FIG. 8 (Table 6) shows an exemplary embodiment of Objectives for the Clinician.

FIG. 9 shows Patient Overall Rating of Improvement of Symptoms used to assess response to treatment.

DETAILED DESCRIPTION OF THE INVENTION

Figure 2:
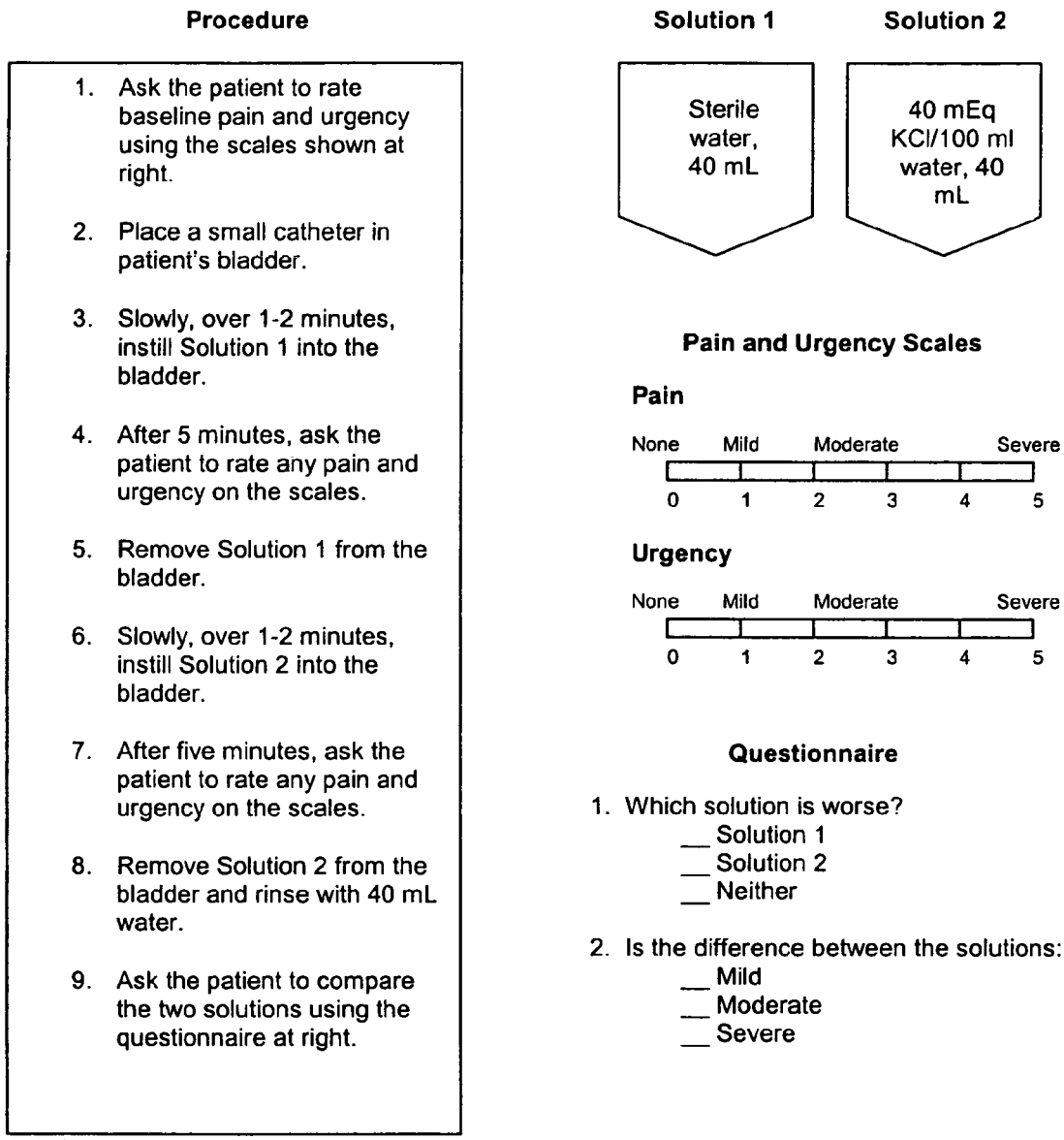
FIG. 2 shows an exemplary embodiment of instructions for performing the Potassium Sensitivity Test (PST).

The present invention relates to a disorder of the lower urinary tract, and in particular, the diagnosis of interstitial cystitis, and reducing the symptoms (including treatment) of interstitial cystitis in vivo. In a preferred embodiment, the present invention relates to compositions and treatment formulations and methods for reducing interstitial cystitis in patients.

In the past, IC was regarded as a rare disease whose symptoms and progression were difficult or impossible to control. It is now believed that IC is a relatively common disorder in both women and men, and that most cases can be treated successfully. In the present invention, detection methods and a novel IC management treatment method that utilizes different combinations of oral and intravesical agents are described.

DEFINITIONS

To facilitate understanding of the invention, a number of terms are defined below.

As used herein including within this specification and the appended claims, the terms "a," "an" and "the" include both singular and plural references, unless the content clearly dictates otherwise.

As used herein, the term "or" when used in the expression "A or B," and where A and B refer to a composition, disease, product, etc., means one, or the other, or both.

The terms "chosen from A, B and C" and "chosen from one or more of A, B and C" are equivalent terms that mean selecting any one of A, B, and C, or any combination of A, B, and C.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b, Unless otherwise indicated, all numbers expressing quantities of ingredients, properties such as molecular weight, reaction conditions, and so forth as used herein, are to be understood as being modified in all instances by the term "about." Accordingly, unless indicated to the contrary, the numerical parameters herein are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

As used herein, "reducing," and "reducing the symptoms of," "reducing interstitial cystitis," and "reducing the symptoms of interstitial cystitis" refers to lowering, lessening and relieving of any one or more of urinary urgency and frequency, and/or pelvic pain. In one embodiment, reducing interstitial cystitis may be determined by the patient. In one embodiment, reducing interstitial cystitis may be determined by the physician's evaluation. In one embodiment, reducing interstitial cystitis may be determined from comparing a PUF scale score to a previous PUF scale score. In some embodiments, reducing interstitial cystitis is reducing symptoms in patients whose symptoms indicate, and are similar to, interstitial cystitis.

As used herein, "liquid" refers to a state of matter in which the substance has definite volume and takes the shape of the container (e.g. solution).

As used herein, "solution" refers to a mixture whose particles can be evenly distributed such that the relative concentrations of the components are the same throughout (e.g. liquid, sol, and the like).

As used herein, "aqueous solution" and "water solution" refers to a solution in which water is the solvent.

As used herein, "therapeutic solution," "therapeutical solution," and "solution for reducing interstitial cystitis," refers to any solution comprising known and potential therapeutic compounds.

As used herein, "pH" refers to a measure of effective concentration of hydrogen ions in a solution (e.g. approximately related to the molarity of $H^+$ by $pH = -\log [H^+]$).

As used herein, "solid" and "solid state" refers to a state of matter in which the substance has definite shape and volume (e.g. powder, crystals, beads, allomer, encapsulated substances, amorphous substances and the like).

As used herein, the term "compound" refers to any chemical entity, pharmaceutical, drug, and the like that may or may not be used be used to treat or prevent a disease, illness, sickness, or disorder of bodily function.

As used herein, the term "therapeutic compounds" comprise both known and potential therapeutic compounds.

As used herein, the term "known therapeutic compound" refers to a compound that has been shown (e.g., through animal trials or prior experience with administration to humans) to be effective in such treatment or prevention.

As used herein, the term "therapeutic" when made in reference to a compound refers to a compound which is capable of reducing, delaying, or eliminating one or more undesirable pathologic effects in a subject.

As used herein, "interstitial cystitis" and "IC" refers to a progressive disorder of the lower urinary tract that causes the symptoms of urinary frequency, urgency, and/or pelvic pain in a wide variety of patterns of presentation. An example of a recent review is Parsons, Clin Obstet Gynecol, 45(1):242-249 (2002).

As used herein, "urinary frequency" refers to the number of urination times per day.

As used herein, "urinary urgency" refers to refers to an inability to delay urination.

As used herein, "pelvic pain" refers to pain in the pelvic region of genital and non-genital origin and of organic or psychogenic aetiology.

As used herein, "urinate," "urination," "urinating," "void" and "voiding" refers to release of urine from the bladder to the outside of the body.

As used herein, "urine" refers to a liquid waste product filtered from the blood by the kidneys, stored in the bladder and expelled from the body through the urethra by the act of urinating.

As used herein, "oral," and "by oral administration" refers to the introduction of a pharmaceutical composition into a subject by way of the oral cavity (e.g. in aqueous liquid or solid form).

As used herein, "oral agent" refers to a compound that can be administered by way of the oral cavity (e.g. in aqueous liquid or solid form). In one embodiment, an oral agent is a heparinoid (e.g. pentosan polysulfate sodium (PPS)).

As used herein, "instill," "instilled," "instillation," refers to one or more of the following; to drop in, to pour in drop by drop, to impart gradually, to infuse slowly, to cause to be imbibed, (e.g. example infuse slowly an intravesical solution).

As used herein, "intravesical," refers to inside the bladder. As such, "intravesical instillation," "intravesical therapy," "instill," and "instillation" refers to solutions that are administered directly into the bladder. In some embodiments, instillation is via catheterization. Further, "intravesical solution," "intravesical agent," "intravesical therapeutic," and intravesical compound" refers to a treatment that can be administered to the bladder. For example, in one embodiment, an intravesical agent is intravesical heparin. In another embodiment, an intravesical agent is PPS. In one embodiment, intravesical therapy is a combination of an oral and an intravesical agent. It is not intended that the present invention be limited to a combination of an oral and an intravesical agent. For example, in one embodiment, intravesical therapy is an intravesical agent. In another embodiment, intravesical therapy is a combination of intravesical agents.

As used herein, "extravesical" refers to outside the bladder.

As used herein, "cystoscopic examination" and "cystoscopy" refers to an examination that uses a cytoscope.

As used herein, "cystoscope" refers to an endoscopic instrument to visualize the lower urinary tract, that includes the bladder and the urethra.

As used herein, "urethra" refers to a tube draining the urine to the outside. As used herein, "bladder" refers to a hollow muscular organ that stores urine until it is excreted from the body.

As used herein, the terms "subject" and "patient" refer to any animal, such as a mammal like a dog, cat, livestock, and a human (e.g. a human with a disease). In one embodiment, a patient has one or more of urinary urgency, urinary frequency, pelvic pain, recurrent urinary tract infections, dyspareunia, overactive bladder, dry, etc.).

As used herein, "urinary tract infections" refers to a condition that includes an inflamed urethra and painful urination. In some embodiments, a urinary tract infection is caused by bacteria. In some embodiments, a urinary tract infection is not caused by bacteria.

As used herein, "recurrent urinary tract infections" refers to frequent episodes of urinary tract infections.

As used herein, "dyspareunia" refers to pain during intercourse.

As used herein, "overactive bladder" refers to a sudden involuntary contraction of the muscular wall of the bladder causing urinary urgency, an immediate unstoppable need to urinate and a form of urinary incontinence.

As used herein, "urinary incontinence" refers to the unintentional loss of urine and inability to control urination or prevent its leakage.

As used herein, "urinary continence" refers to a general ability to control urination.

As used herein, "catheter" refers to a tube passed through the body for draining fluids or injecting them into body cavities. It may be made of elastic, elastic web, rubber, glass, metal, or plastic.

As used herein, "catheterization" refers to the insertion of a slender tube through the urethra or through the anterior abdominal wall into the bladder, urinary reservoir, or urinary conduit to allow urine drainage.

As used herein, "catheterized" refers to the collection of a specimen by a catheterization. The terms "sample" and "specimen" are used in their broadest sense and encompass samples or specimens obtained from any source.

As used herein, the term "biological samples" refers to samples or specimens obtained from animals (including humans), and encompasses cells, fluids, solids, tissues, and gases. Biological samples include tissues (e.g., biopsy material), urine, cells, mucous, blood, and blood products such as plasma, serum and the like. However, these examples are not to be construed as limiting the types of samples which find use with the present invention.

As used herein, the term "urine cytology" refers to an examination of a urine sample that is processed in the laboratory and examined under the microscope by a pathologist who looks for the presence of abnormal cells.

As used herein, "urinary dysfunction" and "urinary tract dysfunction" refers to abnormal urination, patterns or bladder habits, including wetting, dribbling and other urination control problems.

As used herein, "heparinoid" refers to any molecule comprising a "glycosaminoglycan" which refers to a molecule comprising a network of long, branched chains of sugars (e.g. chondroitin sulphate, heparan sulphate, hyaluronic acid, keratin sulphate, dermatan sulphate, hyaluronan and the like) and optimally further comprising smaller, nitrogen-containing molecules (e.g. low molecular weight molecules). It is not meant to limit the present invention to any one glycosaminoglycan (GAG) or source of GAG. GAG molecules include but are not limited to low molecular weight (LMW) GAGs, naturally derived GAGS, biotechnologically prepared GAGS, chemically modified GAGS, synthetic GAGS, and the like. It is not meant to limit the present invention to any one heparinoid molecule or source of heparinoid molecule.

As used herein, "heparin" refers to a heterogeneous group of straight-chain anionic glycosaminoglycans, as described above, having anticoagulant properties with a molecular weight ranging from 2,000 to 40,000 Da. Heparin is measured by its specific anticoagulation activity in units.

As used herein, "anesthesia" refers to a loss of feeling or inability to feel pain.

As used herein, "local anesthesia" refers to a method of pain prevention in a small area of the body.

As used herein, "low-molecular-weight heparins" refers to a lower molecular weight (LMW) species ranging from 2,000-8,000 daltons (e.g., pentosan polysulfate sodium ranging from 4,000-6,000 daltons).

As used herein, the phrases "pharmaceutically acceptable salts", "a pharmaceutically acceptable salt thereof" or "pharmaceutically accepted complex" for the purposes of this application are equivalent and refer to derivatives prepared from pharmaceutically acceptable non-toxic acids or bases including inorganic acids and bases and organic acids and bases.

As used herein, "lower urinary epithelial dysfunction" refers to disorders with positive potassium sensitivity tests (e.g. IC, prostatitis and the like).

As used herein, "urinary dysfunction" refers to abnormal urination, patterns or bladder habits, including wetting, dribbling and other urination control problems.

As used herein, "anticoagulant" refers to delaying or preventing blood coagulation. It is not meant to limit the types of sugars present on a heparin of the present invention. Five examples of sugars occurring in heparin are: (1) α-L-iduronic acid 2-sulfate, (2) 2-deoxy-2-sulfamino-a-D-glucose 6-sulfate, (3) β-D-glucuronic acid, (4) 2-acetamido-2-deoxy-a-D-glucose, and (5) α-L-iduronic acid. Heparin is measured by its specific anticoagulation activity in units.

As used herein, "buffer" refers to a chemical that neutralizes either acids or bases thus stabilizing pH (for example, sodium bicarbonate).

As used herein, "sodium bicarbonate" refers to a compound with the formula $NaHCO$.

As used herein, "base" and "basic solution" refers to a solution whose addition to a second solution aids in providing a specific pH for the combined solution (for example, addition of a sodium bicarbonate solution provides a pH of at least 8.0, as described herein).

As used herein, "normal saline" refers to solutions comprising varying concentrations of sodium chloride (NaCl) in water that are compatible with fluids in the body (e.g. solutions comprising 0.9% NaCl that compatible with the salinity found in most mammalian cells and in human blood). Normal saline will range in pH depending upon the pH of the water used in preparation (e.g. pH of water ranging from 5.5-8.5).

As used herein, "buffered normal saline" refers to a saline solution containing a buffer in order to establish a specific pH value or range (e.g. buffered normal saline with a pH of 7.3 to 7.5 for compatibility with normal human blood). Saline solutions may further comprise sugars (e.g. glucose, dextrose and the like).

As used herein, the term "units" refers to specific activity in International Units (IU) and/or United States Pharmacopeia (USP) units. For example, in one embodiment, heparin contains at least 130 USP units per mg.

As used herein, "USP" unit refers to the quantity of heparin that prevents 1.0 mL of citrated sheep plasma from clotting for 1 hour after the addition of 0.2 mL of 1% $CaCl_2$ at 20 degree C. when compared to a USP reference standard (defined as units/mL).

As used herein, "IU" refers to the quantity of heparin that is active in assays as established by the Fifth International standard for Unfractionated Heparin (WHO-5) (defined as International Units/mL) (Linhardt, R. J. & Gunay, N. S. (1999) Semin Thromb Hemost 25, 5-16.).

In the experimental disclosure which follows, the following abbreviations apply: M (molar); mM (millimolar); μM (micromolar); nM (nanomolar); mol (moles); mmol (millimoles); μmol (micromoles); nmol (nanomoles); g (grams); mg (milligrams); μg (micrograms); pg (picograms); L (liters); mL (milliliters); ml (milliliters); μL (microliters); cm (centimeters); mm (millimeters); μm (micrometers); nm (nanometers); C (degrees Centigrade).

Compositions of the Invention

The compositions of the invention provide a combination of a heparinoid, an anesthetic agent, a buffering compound and, optionally, an osmolar agent, in the manufacture of pharmaceutical compositions for treating IC.

In accordance with the practice of the invention, the composition may be in a solid state or in solution. Preferably, when in solution, the composition has a pH of between 7 and 12.

In one embodiment, the composition comprising a heparinoid, a local anesthetic agent, a buffering compound and an osmolar component are in solution and the osmolar component is present in a sufficient amount so that the final solution is isotonic or near isotonic.

Heparinoid Component of the Compositions of the Invention

The heparinoid in the composition of the invention includes but is not limited to any of heparin, pentosan polysulfate sodium, heparan sulfate, heparin sodium, hyaluronic acid, and chondroitin sulfate, or a combination thereof.

In some embodiments, a heparinoid comprises a heparin-like molecule (e.g. heparan sulfate). For example, a heparin-like molecule such as heparan sulfate is a glycoprotein with a structure similar to heparin with the difference being that heparan sulfate has undergone less polymerization than heparin and so has more glucuronic acid and N-acetyl glucosamine than heparin. Heparan sulfate contains fewer sulfate groups, so is not as effective as an anticoagulant as heparin. Heparin and heparan sulfate are both characterized by repeating units of disaccharides containing a uronic acid (glucuronic or iduronic acid) and glucosamine, which is either N-sulfated or N-acetylated. The sugar residues may be further O-sulfated at the C-6 and C-3 positions of the glucosamine and the C-2 position of the uronic acid. There are at least 32 potential unique disaccharide units in this class of compounds.

Particularly in severe IC, intravesical heparin can be used either alone or in combination with PPS [Parsons, et al. Br J Urol 73:504-507 (1994); Ho, et al. Urology 53:1133-9 (1999)].

Intravesical instillations of hyaluronic acid, a glycosaminoglycan marketed in Canada as Cystistat, may be of benefit for some IC patients. Clinical trials of hyaluronic acid are underway in the United States, but this compound is not approved for U.S. use. The present invention contemplates the substitution of hyaluronic acid for heparin.

In some embodiments, heparin is a higher molecular weight species ranging from 8,000-40,000 daltons. As used herein, "low-molecular-weight heparins" refers to a lower molecular weight (LMW) species ranging from 2,000-8,000 daltons (e.g., pentosan polysulfate sodium ranging from 4,000-6,000 daltons. LMW heparins are made by enzymatic or chemical controlled hydrolysis of unfractionated heparin and have very similar chemical structure as unfractionated heparin except for some changes that may have been introduced due to the enzymatic or chemical treatment. While not intending to limit the mechanism of action of the invention's compositions, the mechanism of action of these drugs may be similar to that of full-length heparin. LMW heparins are usually isolated from bulk heparin.

In one embodiment, heparin or another heparinoid is a heparin salt (e.g. heparin sodium, pentosan polysulfate sodium, heparan sulfate, as in Example 1). As used herein, the phrases "pharmaceutically acceptable salts", "a pharmaceutically acceptable salt thereof" or "pharmaceutically accepted complex" for the purposes of this application are equivalent and refer to derivatives prepared from pharmaceutically acceptable non-toxic acids or bases including inorganic acids and bases and organic acids and bases. Since the compound of the present invention is acidic, salts may be prepared from pharmaceutically acceptable non-toxic bases. A suitable pharmaceutically acceptable counterion for the heparin is a positively-charged counterion such as sodium, calcium, ammonium, and substituted ammonium.

The amount of the heparinoid in the compositions of the invention will vary depending on the subject, severity and course of the disease, the subject's health and response to treatment and the judgment of the treating physician. Accordingly, the dosages of the molecules should be titrated to the individual subject.

For example, for chronic therapy, intravesical heparin can be prescribed at a dose of 10,000-40,000 IU in 10 ml water daily. For maintenance, this same heparin and water solution can be instilled three times weekly, typically on a Monday-Wednesday-Friday schedule [Parsons, et al. Br. J Urol 73:504-507 (1994)]. For immediate relief of IC pain and urgency, heparin can also be used in place of PPS in one embodiment for an intravesical therapeutic solution, which is described below.

For example, in one embodiment, heparin contains at least 130 USP units per mg. As used herein, "USP" unit refers to the quantity of heparin that prevents 1.0 ml of citrated sheep plasma from clotting for 1 hour after the addition of 0.2 ml of 1% $CaCl_2$ at 20 degree C. when compared to a USP reference standard (defined as units/ml). As used herein, "IU" refers to the quantity of heparin that is active in assays as established by the Fifth International standard for Unfractionated Heparin (WHO-5) (defined as International Units/ml) (Linhardt, R. J. & Gunay, N. S. (1999) Semin Thromb Hemost 25, 5-16.).

For example, Pentosan polysulfate sodium (PPS) may be given at a dose of 300 mg per day, although a higher dose may be necessary to obtain a successful result in some cases. For example, for men with IC, PPS may be prescribed at about 600 mg per day, in two or three divided doses.

In accordance with the practice of the invention, merely by way of example, when the heparinoid is heparin, the amount of heparinoid in the composition may be between about 0.5 mg to about 1000 mg of heparin per unit dose (for example about 500 units of heparin to about a maximum of 100,000 units of heparin (e.g., about 1000 USP units to about 100,000 USP units per dose or 100 USP units to about 600 USP units per unit dose of heparin)).

In accordance with the practice of the invention, merely by way of example, when the heparinoid is pentosan polysulfate sodium, the amount of heparinoid in the composition may be about 1 mg to about 600 mg of pentosan polysulfate sodium per unit dose (for example about 100 mg to about 600 mg per unit dose of pentosan polysulfate sodium).

In accordance with the practice of the invention, merely by way of example, when the heparinoid is heparan sulfate, the amount of heparinoid in the composition may be about 0.5 mg to about 10,000 mg of heparan sulfate per unit dose (for example about 100 mg to about 300 mg per unit dose of heparan sulfate).

In accordance with the practice of the invention, merely by way of example, when the heparinoid is hyaluronic acid, the amount of heparinoid in the composition may be about 5 mg to about 600 mg of hyaluronic acid per unit dose (for example about 10 mg to about 100 mg per unit dose of hyaluronic acid).

In accordance with the practice of the invention, merely by way of example, when the heparinoid is chondroitin sulfate, the amount of heparinoid in the composition may be about 1 mg to about 10,000 mg of chondroitin sulfate per unit dose (for example about 100 mg to about 300 mg per unit dose of chondroitin sulfate).

In accordance with the practice of the invention, merely by way of example, when the heparinoid is heparin sodium, the amount of heparinoid in the composition may be about 10 mg to about 600 mg of heparin sodium per unit dose.

In the embodiment of the invention, the patient maybe directed to administer intravesical heparin 40,000 IU in 8 mL of 1% lidocaine and 3 mL of sodium bicarbonate once to twice a day. In one embodiment, this solution is used alone. In some embodiments, this solution is used in combination with PPS (e.g. particularly in cases of severe IC). In some embodiments, intravesical treatment can be added after 9 to 12 months of treatment with oral PPS (e.g. for patients with moderate IC). In some embodiments, the patient administers intravesical heparin (40,000 units) in 8 mL of 1% lidocaine and 3 mL of sodium bicarbonate (see below) once or twice a day (e.g. a combination therapy). In some embodiments, the intravesical medication usually can be tapered slowly and discontinued (e.g. when patients are responding well).

Anesthetic Component of the Compositions of the Invention

The anesthetic (e.g., the local anesthetic) in the compositions of the invention includes but is not limited to any of benzocaine, lidocaine, tetracaine, bupivacaine, cocaine, etidocaine, flecainide, mepivacaine, pramoxine, prilocalne, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof, or a combination thereof. Preferably, the anesthetic (e.g., local anesthetic) is selected from the group consisting of lidocaine, bupivicaine, benzocaine, tetracaine, etidocaine, flecainide, prilocalne, and dibucaine, or a combination thereof. In a preferred embodiment, the local anesthetic comprises at least one of lidocaine, bupivacaine, and mepivacaine. Most preferably, the local anesthetic is lidocaine. The amount of the anesthetic in the compositions of the invention will vary depending on the subject, severity and course of the disease, the subject's health and response to treatment and the judgment of the treating physician. Accordingly, the dosages of the molecules should be titrated to the individual subject. For example, the amount of anesthetic agent in the compositions may be in the range of about 10 mg to about 400 mg per unit dose. For example, the amount of lidocaine can be 10 mL of 1% lidocaine per unit dose or 16 mL of 2% lidocaine per unit dose.

Buffering Compounds of the Compositions of the Invention

The buffering compounds in the compositions of the invention includes but is not limited to bicarbonate buffer, THAM or Tris (Tris(hydroxymethyl)aminomethane) buffer, MOPS buffer (3-(N-morpholino)propanesulfonic acid), HEPES (N-(2-hydroxyethyl)piperazine-N-(2-ethanesulfonic acid) buffer, ACES (2-[(2-amino-2-oxoethyl)amino]ethanoesulfonic acid) buffer, ADA (N-(2-acetamido)2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid) buffer, CHES (2-(N-cyclohexylamino)ethanesulfonic acid) buffer, DIPSO (3-[N,N-bis(2-hydroxyethyl) amino]-2-hydroxy-propanesulfonic acid) buffer, HEPPS(N-(2-hydroxyethylpiperazine)-N'-(3-propanesulfonic acid) buffer, HEPPSO(N-(2-hydroxyethyl)piperazine-N'-(2-hydroxypropanesulfonic acid) buffer, MES (2-(N-morpholino) ethanesulfonic acid) buffer, triethanolamine buffer, imidazole buffer, glycine buffer, ethanolamine buffer, phosphate buffer, MOPSO (3-(N-morpholino)-2-hydroxypropanesulfonic acid) buffer, PIPES (piperazine-N,N'-bis(2-ethanesulfonic acid) buffer, POPSO (piperazine-N,N'-bis(2-hydroxypropaneulfonic acid) buffer, TAPS(N-tris [hydroxymethyl)methyl-3-aminopropanesulfonic acid) buffer; TAPSO (3-[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, and 2-amino-2-methyl-1-propanol buffer. In a preferred embodiment, the buffer is sodium bicarbonate buffer, Tris buffer, phosphate buffer, MOPS buffer, and HEPES buffer, or a combination thereof. In a preferred embodiment, the buffering compound comprises at least one of sodium bicarbonate and THAM (tromethamine or Tris hydroxymethylpropyl). More preferably, the buffering compound is sodium bicarbonate. The amount of the buffering compound in the compositions of the invention will vary depending on the subject, severity and course of the disease, the subject's health and response to treatment and the judgment of the treating physician. Accordingly, the dosages of the molecules should be titrated to the individual subject. For example, the amount of the buffering compound(s) in the compositions of the invention is the amount sufficient to raise the pH of the composition to above about pH 7; preferably above pH 8; or in a range between about pH 7-12. For example, the amount of sodium bicarbonate may be about 3 mL of 8.4% sodium bicarbonate (w/v) per unit dose.

Osmolar Component of the Compositions of the Invention

The therapeutic composition may also contain an osmolar component that provides an isotonic or nearly isotonic solution compatible with human cells and blood. Typically the osmolar component is a salt, such as sodium chloride, or a sugar or a combination of two or more of these components. The sugar may be a monosaccharide such as dextrose, a disaccharide such as sucrose or lactose, a polysaccharide such as dextran 40, dextran 60, or starch, or a sugar alcohol such as mannitol. It should be obvious to those skilled in the art that all components of the composition contribute to the osmolarity of the solution but to achieve an isotonic or near-isotonic solution, the contributions of these components should be taken into account to ensure that the proper osmolar component is added and not added in excess which would result in a hypertonic solution.

Due to the inflamed, permeable nature of the urothelium, a preferred solution would be isotonic or near isotonic. Hypotonic solutions are known to result in cell lysis, particularly of red blood cells, but other cells may also be damaged leading to increased cell damage in the bladder and accessible underlying layers. Hypertonic solutions may result in cell shrinkage which may enlarge pores or weaken cell junctions allowing urinary solutes more access to underlying cell layers leading to further damage, pain and inflammation. The addition of an osmolar component to the composition to form an isotonic or near isotonic solution ensures that neither of these two possibilities occur. Typically, the osmolar component is 0.9% sodium chloride, or somewhat less as the other components in the solution also contribute to the solution's osmolarity and thus should be taken into account. Typically the osmolar component is a salt, such as sodium chloride, or a sugar or a combination of two or more of these components. The sugar may be a monosaccharide such as dextrose, a disaccharide such as sucrose or lactose, a polysaccharide such as dextran 40, dextran 60, or starch, or a sugar alcohol such as mannitol. It should be obvious to those skilled in the art that all components of the composition contribute to the osmolarity of the solution but to achieve an isotonic or near-isotonic solution, the contributions of these components should be taken into account to ensure that the proper osmolar component is added and not added in excess which would result in a hypertonic solution.

The osmolar component of the compositions of the invention includes but is not limited to sodium chloride, dextrose, dextran 40, dextran 60, starch and mannitol, or a combination thereof.

The amount of the osmolar component in the compositions of the invention will vary depending on the subject, severity and course of the disease, the subject's health and response to treatment and the judgment of the treating physician. Accordingly, the dosages of the molecules should be titrated to the individual subject. For example, the amount of the osmolar component(s) in the compositions of the invention is at least 50 milliosmoles.

Additional embodiments of the invention include pharmaceutical compositions comprising the composition of the invention and a pharmaceutically acceptable carrier.

Examples of suitable pharmaceutical carriers and adjuvants include any material which when combined with the components of the compositions of the invention retain the component's activity, and is non-reactive with the subject's immune system. These carriers and adjuvants include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g. oil/water emulsion), salts or electrolytes such as, disodium hydrogen phosphate, sodium chloride, zinc salts, colloidal silica, magnesium trisilicate, polyvinyl pyrrolidone, cellulose-based substances and polyethylene glycol. Other carriers may also include sterile solutions. Compositions comprising such carriers are formulated by well known conventional methods. Such compositions may also be formulated within various lipid compositions, such as, for example, liposomes as well as in various polymeric compositions, such as polymer microspheres.

In a further embodiment, the present invention provides pharmaceutical compositions for inhibiting Interstitial Cystitis and its symptoms in a subject. In an embodiment, the pharmaceutical composition comprises a heparinoid, which composition may be administered together with a pharmaceutical composition comprising a local anesthetic agent and a pharmaceutical composition comprising a buffering compound and optionally a pharmaceutical composition comprising an osmolar agent that provides an isotonic or nearly isotonic solution, for example, compatible with human cells and blood. The aforementioned pharmaceutical compositions may be administered concomitantly or in sequence.

In another embodiment, the order of administration of the heparinoid and the local anesthetic agents can be switched such that the local anesthetic agent is administered with a heparinoid and a buffering compound and optionally an osmolar agent, or, the buffering compound is administered with a local anesthetic agent and a heparinoid and optionally an osmolar component. A description of the heparinoids, local anesthetic agents, buffering compounds and osmolar components are detailed above.

In a further embodiment of the invention, the present invention provides kits (e.g., a packaged combination of reagents with instructions) containing the compositions of the invention or components of the composition of the invention useful for treating Interstitial Cystitis and/or the symptoms of IC. The kit may further comprise a label indicating that the heparinoid, the anesthetic agent and the buffering compound are useful to treat Interstitial Cystitis.

The kit can contain a pharmaceutical composition that includes the compositions of the invention, and an acceptable carrier or adjuvant, e.g., pharmaceutically acceptable buffer, such as phosphate-buffered saline, Ringer's solution and dextrose solution. It may further include other materials desirable from a commercial and user standpoint, including other buffers, diluents, filters, needles, syringes, and package inserts with instructions for use. The composition may be provided as dry powders, usually lyophilized, including excipients that upon dissolving will provide a reagent solution having the appropriate concentration.

The kit comprises a container with a label and/or instructions. Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle). The container can hold the composition(s) of the invention for treating IC.

In another embodiment, the kit comprises multiple containers, one for each of the components of the compositions of the invention and/or a pharmaceutically acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The kit may also suitably include a label and/or instructions on, or associated with the container. The label can provide directions for carrying out the preparation of the components of the compositions of the invention, for example, dissolving of the dry powders, and/or treatment for IC.

The label and/or the instructions can indicate directions for either in vivo or in vitro use of the compositions or pharmaceutical compositions of the invention. The label and/or the instructions can indicate that the composition or pharmaceutical composition is used alone, or in combination with other agents.

The label can indicate appropriate dosages for the molecules of the invention. The label and/or the instructions can also indicate that the pharmaceutical composition can be used alone, or in combination, with a other agent to treat e.g., IC or the symptoms of IC.

In an embodiment, the present invention provides products (for example kit-of-parts) containing a heparinoid, a local anesthetic agent, a buffering compound and optionally an osmolar component, as a combined preparation for simultaneous, separate or sequential use, in inhibiting Interstitial Cystitis and its symptoms in a subject.

Methods of the Invention

The invention also provides methods for inhibiting Interstitial Cystitis in a subject. The method comprises administering an effective amount of the compositions of the invention to the subject to inhibit IC and its symptoms in the subject. In accordance with the foregoing, the present invention provides in a yet further aspect methods as defined above comprising co-administration, e.g. concomitantly or in sequence, of a therapeutically effective amount of a heparinoid, a local anesthetic agent, and a buffering compound or a heparinoid, a local anesthetic agent, a buffering compound, and an osmolar component in free form or in pharmaceutically acceptable salt form to inhibit IC and its symptoms in the subject. The composition may be administered in solid state or in solution. Administration may be effected by any of the following means: intravesicular administration, administration by means of biodegradable polymers, administration by means of hydrogels, and administration through dual chamber syringes.

A description of the heparinoids, anesthetics, buffering compounds and osmolar components is detailed above.

The most effective mode of administration and dosage regimen for the compositions of the present invention depends upon the severity and course of the disease, the subject's health and response to treatment and the judgment of the treating physician. Accordingly, the dosages of the molecules should be titrated to the individual subject.

Adjustments in the dosage regimen may be made to optimize the IC inhibiting response. Doses may be divided and administered on a daily basis or the dose may be reduced proportionally depending upon the situation. For example, several divided doses may be administered daily or the dose may be proportionally reduced as indicated by the specific therapeutic situation.

Merely by way of example, the amount of heparinoid may be between about 0.5 mg to about 1000 mg of heparin per unit dose (for example about 1000 USP units to about 100,000 USP units per dose or 100 USP units to about 600 USP units per unit dose of heparin), about 1 mg to about 600 mg of pentosan polysulfate sodium per unit dose (for example about 100 mg to about 600 mg per unit dose of pentosan polysulfate sodium), about 0.5 mg to about 10,000 mg of heparan sulfate per unit dose (for example about 100 mg to about 300 mg per unit dose of heparan sulfate), about 5 mg to about 600 mg of hyaluronic acid per unit dose (for example about 10 mg to about 100 mg per unit dose of hyaluronic acid), about 1 mg to about 10,000 mg of chondroitin sulfate per unit dose (for example about 100 mg to about 300 mg per unit dose of chondroitin sulfate), or about 10 mg to about 600 mg of heparin sodium per unit dose. Additional dosages may be found supra. It would be clear to one skilled in the art that dosage will vary depending on the particular heparinoid being used.

The description of the local anesthetic is detailed above. An attending physician will determine specific dosages of the local anesthetic for each subject. The amount of lidocaine may be 10 mL of 1% lidocaine per unit dose or 16 mL of 2% lidocaine per unit dose. Additional dosages may be found supra. The amount of local anesthetic will vary depending on the local anesthetic being used.

The description of the buffering compound is detailed above. The sodium bicarbonate may be 3 mL of 8.4% sodium bicarbonate (w/v) per unit dose. Additional dosages may be found supra. Since the buffering compound increases the absorbance of the local anesthetic agent, the amount of buffering compound will vary depending on the buffering compound and the local anesthetic agent being used.

The description of the osmolar component is detailed above. Dosages may be found supra. An attending physician will determine specific dosages of the osmolar component for each subject. The osmolar component is present in a sufficient amount so that the final solution is isotonic or near isotonic.

Pentosan polysulfate sodium may be formulated for oral administration and may be administered in a quantity from about 100 mg/day to about 600 mg/day or in a quantity from about 100 mg/day to about 300 mg/day. Additional dosages may be found supra.

In accordance with the foregoing, the present invention provides methods for repairing a mucin layer of bladder tissue thereby inhibiting Interstitial Cystitis. The method comprising co-administration, e.g. concomitantly or in sequence, of a therapeutically effective amount of heparinoid, local anesthetic agent, buffering compound and osmolar component or the compositions of the invention.

The subjects treated by the present invention include mammalian subjects, including, human, monkey, ape, dog, cat, cow, horse, goat, pig, rabbit, mouse and rat.

In accordance with the foregoing, the present invention provides methods for monitoring the course of Interstitial Cystitis in a subject comprising intravesicular administration of a solution containing an amount of potassium that would elicit pain in a subject that has a compromised urothelium and monitoring their pain response at different points in time, a difference in the amount of pain determined being indicative of the course of the Interstitial Cystitis condition, wherein the subject has been administered any of the compositions of the invention.

In another embodiment, the method for monitoring comprises quantitatively determming in a first sample of a biological fluid from the subject the amount of potassium and comparing the amount so determined with the amount present in a second sample from the subject, such samples being taken at different points in time, a difference in the amounts determined being indicative of the course of the Interstitial Cystitis condition, wherein the subject has been administered the compositions of the invention.

In accordance with the practice of the invention, examples of heparinoid include but are not limited to heparin, pentosan polysulfate sodium, heparan sulfate, hyaluronic acid, chondroitin sulfate and heparin sodium, or a combination thereof; examples of anesthetic agent include but are not limited to lidocaine, bupivacaine, and mepivacaine, or a combination thereof; examples of buffering compound include but are not limited to bicarbonate and THAM (tromethamine or Tris hydroxymethylpropyl), or a combination thereof and suitable examples of an osmolar component include but are not limited to sodium chloride, dextrose, dextran 40, dextran 60, starch and mannitol, or a combination thereof.

In a further aspect of the above uses, the heparinoid, anesthetic agent, buffering compound and osmolar agent can be administered concomitantly or in sequence.

A description of the amounts of the heparinoid, anesthetic agent, buffering compound and osmolar agent is provided supra. An attending physician may determine specific dosages of the heparinoid, anesthetic agent, buffering compound and osmolar agent, for each subject.

Advantages of the Invention

The available data indicate that the size of the potential market for the compounds used in the multimodal IC treatment approach is quite large. The most current estimate of the true prevalence of IC is that the disease affects as many as 1 in 4.5 women [Parsons, et al. Urology 60:573-578 (2002)] and 1 in 20 men [Nickel, et al. J Urol. 165:842-845 (2001)] in the United States. In our extensive clinical experience, the multimodal treatment regimen is effective in up to 85-90% of cases of IC. The current prevalence estimates come from true prevalence studies in which a general population was screened for the characteristic symptom complex of IC. Previous prevalence studies have focused on screening a population for individuals who have already received a diagnosis of IC, and have used diagnostic criteria that recognized only the fraction of the IC patient population that has severe, advanced disease.

The number of identified cases of IC is likely to grow substantially as more and more clinicians recognize IC as the actual cause in patients whose symptoms initially had been attributed to other problems.

Until recently, the diagnosis of IC was based on criteria, originally developed for research purposes, (Gillenwater and Wein, J Urol 140(1):203-206 (1988)) which describe the relatively rare case of advanced disease. A case of IC usually was not recognized until it was quite severe and had produced bladder lesions that could be seen by cystoscopic examination. As knowledge about IC has grown, the medical community has become much better able to detect mild or moderate disease, which responds to available therapies in most cases.

In IC, the goal of therapy is to achieve control of the disease symptoms while addressing the underlying cause(s) of the disorder. The invention resolves symptoms of pain and urgency by neural desensitization by e.g., the alkalinized lidocaine—the underlying urothelium integrity is improved by the heparin sodium.

The following examples serve to illustrate certain embodiments and aspects of the present invention and are not to be construed as liming the scope thereof.

EXAMPLE 1

The IC treatment approach described under Current Practice below represents a therapeutic paradigm of the present invention for IC/LUDE. This paradigm reflects a volume of research and clinical data that has revolutionized our concept of IC pathogenesis, diagnosis, and treatment in recent years. Traditionally considered rare and difficult to manage, IC is now known to be relatively common and highly treatable.

Recognizing IC

Until recently, the diagnosis of IC was based on criteria, originally developed for research purposes, (Gillenwater and Wein, J Urol 140(1):203-206 (1988)) which describe the relatively rare case of advanced disease. A case of IC usually was not recognized until it was quite severe and had produced bladder lesions that could be seen by cystoscopic examination. As used herein, "cystoscopic examination" and "cystoscopy" refers to an examination that uses a cytoscope. As used herein, "cystoscope" refers to an endoscopic instrument to visualize the lower urinary tract that includes the bladder and the urethra. As used herein, "urethra" refers to a tube draining the urine to the outside. As used herein, "bladder" refers to a hollow muscular organ that stores urine until it is excreted from the body. As knowledge about IC has grown, the medical community has become much better able to detect mild or moderate disease, which responds to available therapies in most cases.

The diagnosis of IC is relatively simple if the clinician takes the following approach: look for the characteristic pattern of IC symptoms (Table 1) in the appropriate clinical setting, rule out other definable causes of the patient's urgency/frequency and/or pelvic pain and rely on the potassium sensitivity test (PST; described below) to confirm the diagnosis.

The symptoms of IC tend to occur in a pattern of sudden flares followed by remissions, with the flares becoming more severe and more continuous as the disease progresses. Moderate to severe IC can severely impair a patient's physical, emotional, social, and professional life. Several clinical situations should alert the physician that IC might be present. One example is women with recurrent urinary tract infections. Usually these episodes are IC flares, as shown by negative urine cultures. Another example are women or men with dyspareunia; most will have IC. Another example is women with a diagnosis of "overactive bladder, dry." Most likely, these patients have IC. As used herein, the terms "subject" and "patient" refer to any animal, such as a mammal like a dog, cat, livestock, and a human (e.g. a human with a disease). In one embodiment, a patient has one or more of urinary urgency, urinary frequency, pelvic pain, recurrent urinary tract infections, dyspareunia, overactive bladder, dry, etc. As used herein, "urinary tract infections" refers to a condition that includes an inflamed urethra and painful urination. In some embodiments, a urinary tract infection is caused by bacteria.

In some embodiments, a urinary tract infection is not caused by bacteria. As used herein, "recurrent urinary tract infections" refers to frequent episodes of urinary tract infections. As used herein, "dyspareunia" refers to pain during intercourse. As used herein, "overactive bladder" refers to a sudden involuntary contraction of the muscular wall of the bladder causing urinary urgency, an immediate unstoppable need to urinate and a form of urinary incontinence. As used herein, "urinary incontinence" refers to the unintentional loss of urine and inability to control urination or prevent its leakage. As used herein, "urinary continence" refers to a general ability to control urination.

Urgency/frequency is not always present in an individual with IC. Even if a patient urinates more than 8 times in 24 hours, the frequency may have developed so gradually that he or she has not recognized it as abnormal. A 24-hour voiding log or the Pelvic Pain and Urgency/Frequency (PUF) Scale (described in the following section) or both are useful in obtaining a true picture of the patient's voiding patterns.

The pain of IC, rather than symptoms of urgency/frequency, is what usually brings a patient to the doctor. The location of the pain is what guides the patient to choose either a urologist or a gynecologist. Unfortunately, the pain does not necessarily point to the origin of the problem, which is the lower urinary tract. A patient with IC may perceive the pain anywhere in the pelvis, in 1 or more locations in any combination (Table 1). IC pain often includes pain during or immediately after sexual intercourse. A number of factors can influence the severity of a patient's symptoms on any given day (Table 2). Thus, IC is extremely variable in its presentation; its symptoms can be mistaken for signs of a different urologic or gynecologic problem. However, it is important to detect this condition because effective therapy is available, and early cases respond more readily to treatment than do advanced cases.

Diagnostic Tools

IC should be suspected in any man or woman who presents with urinary urgency/frequency and/or pelvic pain in the absence of any other definable cause. Several simple diagnostic tools can help the clinician rule out other causes of the patient's complaints and establish the likelihood of the presence of IC.

Rule Out Other Problems

A simple urinalysis, and a urine culture if indicated, are the only tests required to rule out most other problems that should be considered in a patient with the symptoms of IC. A voided urine specimen should be obtained for analysis. Because patients with IC often void low volumes, if the voided specimen is not negative, it is optimal to obtain a catheterized urine specimen for analysis (Brendler, In: Walsh, et al, eds., Campbell's Urology, 7th ed. Philadelphia, Pa.: W B Saunders Co; 144 (1998)). An IC patient's catheterized specimen should show no bacteria and probably will show no red or white blood cells. As used herein, "catheter" refers to a tube passed through the body for draining fluids or injecting them into body cavities. It may be made of elastic, elastic web, rubber, glass, metal, or plastic. As used herein, "catheterization" refers to the insertion of a slender tube through the urethra or through the anterior abdominal wall into the bladder, urinary reservoir, or urinary conduit to allow urine drainage. As used herein, "catheterized" refers to the collection of a specimen by a catheterization. The terms "sample" and "specimen" are used in their broadest sense and encompass samples or specimens obtained from any source. As used herein, the term "biological samples" refers to samples or specimens obtained from animals (including humans), and encompasses cells, fluids, solids, tissues, and gases. Biological samples include tissues (e.g., biopsy material), urine, cells, mucous, blood, and blood products such as plasma, serum and the like. However, these examples are not to be construed as limiting the types of samples which find use with the present invention.

If urinalysis reveals gross or microscopic hematuria, the presence of malignancy should be ruled out via a complete urologic workup. Any male over age 40 should undergo a urine cytology and an office cystoscopy. Individuals who are at high risk for cancer should be identified and evaluated according to standard urologic practice. As used herein, the term "urine cytology" refers to an examination of a urine sample that is processed in the laboratory and examined under the microscope by a pathologist who looks for the presence of abnormal cells.

PUF Scale

The questionnaire of the present invention is designed to elicit a balanced picture of a patient's IC symptoms (FIG. 1). It has been validated in both urologic and gynecologic patients with pelvic pain, most of whom were determined to have IC (Parsons, et al. Urology 60(4):573-578 (2002)). There appears to be a strong correlation between a patient's PUF score and his or her chance of having a positive result on the PST (FIG. 1). The PUF Scale is useful in screening male and female patients for the presence of IC symptoms. The higher the PUF score, the greater the likelihood that the patient has IC (Table 3).

Potassium Sensitivity Test

The intravesical PST, which can be performed in a clinician's office, is useful in establishing the diagnosis of IC (Parsons, et al. Neurourol Urodyn 13(5):515-520 (1994); Parsons, et al. J Urol 159(6):1862-1867 (1998); Parsons, et al. Urology 59(3):329-333 (2002)). A number of recent studies indicate that the PST is a sensitive and reliable indicator of the presence of the disease (Parsons, et al. Neurourol Urodyn 13(5):515-520 (1994); Parsons, et al. J Urol 159(6):1862-1867 (1998); Parsons et al. Urology 59(3):329-333 (2002); Parsons and Albo, J Urol 168(3):1054-1057 (2002)).

The PST detects a lower urinary tract dysfunction that appears to be present in most individuals with IC (Parsons, et al. J Urol 145(4):732-735 (1991). As used herein, "urinary dysfunction" and "urinary tract dysfunction" refers to abnormal urination, patterns or bladder habits, including wetting, dribbling and other urination control problems. This dysfunction of the epithelial defense mechanisms results in an abnormally permeable epithelium that fails to protect the underlying tissues from potentially damaging substances in the urine; chiefly, potassium. If urinary potassium is allowed to penetrate the epithelium, it can depolarize nerves and muscle and cause the symptoms of urinary urgency or pain (or both) as well as tissue damage (Parsons et al. J Urol 159(6):1862-1867 (1998)).

For the PST, two separate solutions, sterile water and potassium chloride are instilled via a catheter into the patient's bladder (Parsons, et al. Urology 2002; 59(3):329-333). An individual with normal bladder epithelial defense mechanisms experiences no symptoms in response to the potassium solution. However, in a person with an abnormally permeable epithelium, the potassium solution provokes symptoms of urgency or pain or both. FIG. 2 provides instructions for performing the PST.

The patient uses a numeric analog scale to grade any pain or urgency that results from the instillation of each solution. After both solutions have been instilled, the patient is asked to indicate which solution caused more severe symptoms. If the patient's urgency or pain grade is at least 2 points above 0 and the patient indicated that the potassium solution provoked more severe symptoms, the PST result is positive.

IC is a Common Disorder

Although IC originally was believed to be rare, the latest data suggest that it is quite common. The earliest prevalence data reflected the traditional IC diagnostic criteria (Gillenwater, et al. J Urol 1988; 140(1):203-206 (1987)) and probably excluded all but advanced cases of the disease. In 1999, prevalence in the United States was estimated at 750,000 cases (Curhan, et al. J Urol 161(2):549-552 (1999)). Even this more recent figure does not reflect the true prevalence of IC because it includes only diagnosed cases. It probably does not include most mild to moderate cases, which go undetected or are mistaken for other problems.

Prevalence in Women

In a study reported last year, gynecologists from several clinical practices in the United States found strong evidence that there are large numbers of unrecognized cases of IC among their chronic pelvic pain (CPP) patients (Parsons, et al. Obstet Gynecol 98(1):127-132 (2001); Parsons, et al. Am J Obstet Gynecol 187(5):1395-1400 (2002). The rate of positive PST results among 114 pelvic pain patients was 85% (Parsons, et al. Obstet Gynecol 98(1):127-132 (2001)). These findings were confirmed in a larger follow-up study with controls, in which the PST result was positive in 198 (81%) of 244 pelvic pain patients and in none of the controls. As the size of the nation's CPP patient population has been estimated at 9 million women or more, (Mathias, et al. Obstet Gynecol 87(3):321-327 (1996)) these findings suggest that the number of IC patients may be at least 10 times higher than the estimate published in the most recent epidemiologic study (Curhan, et al. J Urol 161(2):549-552(1999). If this is the case, at least 7 million women in the United States may have IC. The data showing a high prevalence of IC were further corroborated by the results of a study in which a sample population of women was surveyed using the PUF Scale (Parsons, et al. Urology 60(4):573-578 (2002)). In this study, 1 of every 4 women had a PUF score that predicted the presence of IC.

Prevalence in Men

Findings from two recent studies suggest that unsuspected numbers of male patients have IC, (Parsons and Albo, J Urol 168(3):1054-1057 (2002); Bernie, et al. J Urol 166(1):158-161 (2001)). PST results were positive in 37 (84%) of 44 men who had been diagnosed with prostatitis (Parsons and Albo, J Urol 168(3):1054-1057 (2002)) and in 84 (16%) of 526 men who were undergoing urodynamic evaluation for possible bladder outlet obstruction due to benign prostatic hyperplasia (Bernie, et al. J Urol 166(1):158-161 (2001)). In the latter study, the PST-positive men also demonstrated urodynamics results similar to those characteristic of IC.

Treatment

Most patients with IC will benefit from a three-part plan for medical treatment (Table 4) that focuses on the following: restoring lower urinary tract epithelial function with heparinoid therapy; reversing neural activation with tricyclic antidepressant therapy; and controlling allergies with antihistamine therapy.

Once other disorders have been ruled out (as described in the previous section), treatment should not be withheld from a patient who has signs and symptoms of IC but who has negative results from the intravesical PST. If the physician's clinical impression is that a patient has IC, the patient should be started on IC therapy as described here.

Restoring Lower Urinary Tract Epithelial Function

For most IC patients, the cornerstone of treatment comprises a heparinoid therapy with oral pentosan polysulfate sodium (Parsons, et al. J Urol 150(3):845-848 (1993); Mulholland, et al. Urology 35(6):552-558 (1990); Parsons and Mulholland, J Urol. 138(3):513-516 (1987); Holm-Bentzen, et al. J Urol 138(3):503-507 (1987); Hanno, Urology 49 (5A suppl):93-99 (1997); Nickel, et al. J Urol 165(suppl 5):67 Abstract 273, (2001)) (PPS; ELMIRON, Ortho-McNeil/Alza), intravesical heparin, (Parsons, et al. Br J Urol 73(5): 504-507 (1994)) or both. Heparinoids are similar in structure to the glycosaminoglycans in the bladder surface mucus and are believed to help repair or restore the epithelium (Parsons, Urology 49(5A suppl):100-104 (1997) in individuals who have abnormal epithelial permeability. As used herein, "heparinoid" refers to any molecule comprising a "glycosaminoglycan" which refers to a molecule comprising a network of long, branched chains of sugars (e.g. chondroitin sulphate, heparan sulphate, hyaluronic acid, keratin sulphate, dermatan sulphate, hyaluronan and the like) and optimally further comprising smaller, nitrogen-containing molecules (e.g. low molecular weight molecules). Glycosaminoglycan also refers to "mucopolysaccharide." It is not meant to limit the present invention to any one glycosaminoglycan (GAG) or source of GAG. GAG molecules include but are not limited to low molecular weight (LMW) GAGs, naturally derived GAGS, biotechnologically prepared GAGS, chemically modified GAGS, synthetic GAGS, and the like. It is not meant to limit the present invention to salts (e.g. sodium sale, calcium salt and the like) and sulfates and includes other forms of these molecules. It is not meant to limit the present invention to any one heparinoid molecule or source of heparinoid molecule. In some embodiments, a heparinoid comprises a heparin-like molecule (e.g. heparan sulfate). For example, a heparin-like molecule such as heparan sulfate is a glycoprotein with a structure similar to heparin with the difference being that heparan has undergone less polymerization than heparin and so has more glucuronic acid and N-acetyl glucosamine than heparin. Heparan contains fewer sulfate groups, so is not as effective as an anticoagulant as heparin. Heparin and heparan sulfate are both characterized by repeating units of disaccharides containing a uronic acid (glucuronic or iduronic acid) and glucosamine, which is either N-sulfated or N-acetylated. The sugar residues may be further O-sulfated at the C-6 and C-3 positions of the glucosamine and the C-2 position of the uronic acid. There are at least 32 potential unique disaccharide units in this class of compounds. In some embodiments, a heparinoid comprises a heparin molecule (e.g. a heparin sodium), a pentosan polysulfate sodium (PPS) and the like. As used herein, "heparin" refers to a heterogeneous group of straight-chain anionic glycosaminoglycans, as described above, having anticoagulant properties with a molecular weight ranging from 2,000 to 40,000 Da.

In some embodiments, heparin is a higher molecular weight species ranging from 8,000-40,000 daltons. As used herein, "low-molecular-weight heparins" refers to a lower molecular weight (LMW) species ranging from 2,000-8,000 daltons (e.g., pentosan polysulfate sodium ranging from 4,000-6,000 daltons. LMW heparins are made by enzymatic or chemical controlled hydrolysis of unfractionated heparin and have very similar chemical structure as unfractionated heparin except for some changes that may have been introduced due to the enzymatic or chemical treatment. While not intending to limit the mechanism of action of the invention's compositions, it is the inventor's view that mechanism of action of these drugs is similar to that of full-length heparin. LMW heparins are usually isolated from bulk heparin. In one embodiment, heparin is a heparin salt (e.g. heparin sodium, pentosan polysulfate sodium, heparan sulfate). As used herein, the phrases "pharmaceutically acceptable salts", "a pharmaceutically acceptable salt thereof" or "pharmaceutically accepted complex" for the purposes of this application are equivalent and refer to derivatives prepared from pharmaceutically acceptable non-toxic acids or bases including inorganic acids and bases and organic acids and bases. Since the compound of the present invention is acidic, salts may be prepared from pharmaceutically acceptable non-toxic acids. A suitable pharmaceutically acceptable counterion for the heparin is a positively-charged counterion such as sodium, calcium, ammonium, and substituted ammonium.

Recent data indicate that PPS is the most effective treatment available for IC (Hanno, Urology 49 (5A suppl):93-99 (1997); Nickel et al. J Urol 165(suppl 5):67. Abstract 273 (2001). These longitudinal open-label studies have shown that the response rate increases with increasing duration of treatment, reaching approximately 70% after 8 to 12 months of therapy (Hanno, Urology 49 (5A suppl):93-99 (1997); Nickel et al. J Urol 165 (suppl 5):67. Abstract 273, (2001)) PPS typically is given at a dose of 300 mg per day, although a higher dose may be necessary to obtain a successful result in some cases. For men with IC, PPS, 600 mg per day, (off-label use), in two or three divided doses is routinely prescribed. It should be noted that prescribing PPS at a dose above 300 mg/day is an off-label use of the drug.

In the embodiment of the invention, the patient is directed to administer intravesical heparin 40,000 IU in 8 mL, 1% lidocaine, and 3 mL of sodium bicarbonate once to twice a day. In one embodiment, this solution is used alone. In some embodiments, this solution is used in combination with PPS (e.g. particularly in cases of severe IC). In some embodiments, intravesical treatment can be added after 9 to 12 months of treatment with oral PPS (e.g. for patients with moderate IC). In some embodiments, the patient administers intravesical heparin (40,000 units) in 8 mL of 1% lidocaine and 3 mL of sodium bicarbonate (see below) once or twice a day (e.g. a combination therapy). In some embodiments, the intravesical medication usually can be tapered slowly and discontinued (e.g. when patients are responding well).

Symptoms of urgency and pain can persist in an IC patient after the epithelium has been restored because it takes time for upregulated bladder nerves to deactivate. The results of heparinoid therapy should be judged only after at least 1 year of treatment in a patient with mild to moderate disease and only after at least 2 years of treatment in a patient with severe IC.

Treatment for Immediate Relief of Symptoms

Encouraging data were obtained from a preliminary study of an intravesical solution for the immediate and sustained relief of the symptoms of urgency and pain in IC patients. The solution contains 40,000 units of heparin or 100 mg PPS, 80 mg of lidocaine, and 3 mL of sodium bicarbonate (see below) in a total fluid volume of 15 mL. The absorption of the lidocaine is increased by the presence of the sodium bicarbonate, which is the principal difference between the therapeutic solution of the present invention and other similar solutions that have been tried.

In the preliminary study, 31 (78%) of 40 patients experienced significant immediate relief of their IC symptoms. Of the patients who used the solution 3 to 7 times weekly for 2 weeks or more, 85% had sustained pain relief. If further studies confirm these promising initial results, this solution will be the first treatment to offer immediate relief of the pain and urgency of IC.

Goal of Therapy

In IC, the goal of therapy is to achieve control of the disease symptoms while addressing the underlying cause(s) of the disorder. The invention resolves symptoms of pain and urgency by neural desensitization by the alkalinized lidocaine—the underlying urothelium integrity is improved by the heparin sodium. With the guidance of the physician, the patient should make his or her own treatment decisions. In the treatment process, it is important for the clinician to help the patient develop an understanding of what to expect from the disease and from the treatment over the long term. Many IC patients have suffered for years before finding a physician who recognizes the source of their symptoms.

Achieving Control of Symptoms

The IC symptoms of frequency, urgency, and pelvic pain present differently among patients who have IC, and can vary from one day to the next in a single affected individual. IC is a progressive disorder that tends to present as a series of flares and remissions in its early stages. Typically, IC symptoms do not become both severe and continuous until the disease has been present for many years [Parsons, et al. Urology 57:428-33 (2001); Hand, J Urol 61:291-310 (1949); Parsons, Neurourol Urodyn 9:241-50 (1990); and Koziol, et al. J Urol 149:465-9 (1993)].

A patient may perceive IC pain as dysuria and/or as pain in the suprapubic area, the lower abdomen, the lower back, the medial thighs, the inguinal area, the urethra, the vagina or vulva in women, and the scrotum or testes in men [Parsons, et al. Urology 57:428-33 (2001); Hand, J Urol 61:291-310 (1949)]. A given patient may experience pain in one or more of these locations, in any combination. Recent studies suggest there are significant numbers of IC patients in the populations of men and women who seek treatment for chronic pelvic pain [Parsons, et al. Urology 60:573-578 (2002); Parsons, et al. Am. J. Obstet Gynecol 187:1395-1400 (2002); Parsons and Albo, J Urol 168:1054-1057 (2002)]. Approximately 3 out of 4 IC patients, both male and female, have pain associated with sexual activity. Pain may be the patient's only symptom of IC, as some IC patients experience no urinary urgency/frequency. In my clinical experience, a female patient who has dyspareunia and chronic pelvic pain has an 80% chance of having a genitourinary source for that pain, regardless of where in the pelvis the pain is perceived.

It is well known that a number of factors provoke flares of IC symptoms in affected individuals. These include hormonal fluctuations, the activity of seasonal allergies, physical stress, emotional stress, and sexual activity [Parsons, et al. Urology 57:428-33 (2001); Parsons, Neurourol Urodyn 9:241-250 (1990); Koziol, Urol Clin North Am. 21:7-71 (1994); Held, et al. in Interstitial Cystitis, Hanno, et al (Eds), Springer-Verlag, London, p: 29-48 (1990)]. In addition, a patient's symptoms will depend on the lower urinary tract tissues affected by the disease. There is increasing evidence that IC is part of a larger disorder that can be called Lower Urinary Dysfunctional Epithelium (LUDE) [Parsons, et al. Urology 57:428-33 (2001); Parsons, et al. Urology 60:573-578 (2002); Parsons, et al. Am J Obstet Gynecol 187:1395-1400 (2002); Parsons and Albo, J Urol 168:1054-1057 (2002)]. LUDE can affect the bladder, the urethra, and (in men) the prostate. For all of these reasons, it is more accurate to regard IC as a continuum than as a disease with a single, characteristic clinical presentation.

In the effort to provide symptom relief for the IC patient, an important first step is to identify and quantify all of the IC symptoms from which the patient currently suffers. A recently validated IC symptom questionnaire of the present invention, the Pelvic Pain and Urgency/Frequency Patient Symptom Scale (PUF Scale, FIG. 1) can be extremely useful for this purpose [Parsons, et al. Urology 60:573-578 (2002)]. The PUF Scale is a self-administered questionnaire that can be completed by the patient in less than 5 minutes. It contains questions that elicit and quantify urinary frequency and/or urgency (if any), pelvic pain, and/or pain associated with sexual activity. The result is a single numeric score from 0 through 35. The higher the PUF score, the greater the likelihood that the individual has IC [Parsons, et al. Urology 60:573-578 (2002)]; for this reason, the PUF can be useful in distinguishing IC from other disorders during the process of diagnosis.

A patient's responses on the PUF Scale also may make the clinician aware of any IC symptoms the patient may experience but may not recognize as abnormal. Individuals who have urinary frequency (that is, voiding 8 or more times per day) may not report it as a problem because it has always been normal for them, or does not worry them. Nevertheless, it is a symptom that indicates the presence of a pathophysiologic process that must be recognized so that treatment can be initiated as early as possible in the disease process. Frequency is typically the first symptom to appear in an individual who has IC. Urinary urgency often follows, and pain tends to be a later manifestation of the disease. In clinical experience, pain—especially acute pain—usually is the symptom that prompts the patient to seek treatment for IC.

Addressing an Underlying Cause of IC

Bladder epithelial permeability and urinary potassium appear to play a key role in the development of many cases of the disease [Parsons, et al. J Urol 159:1862-1867 (1998)]. In the healthy bladder, a mucus layer containing glycosaminoglycans (GAGs) forms a barrier that prevents urine and its contents from leaking through the urothelium and damaging the underlying nerves and muscle [Lilly and Parsons, Surg Gynecol Obstet 171:493-496 (1990)]. Most individuals with IC have an epithelial dysfunction that renders the urothelium abnormally permeable. As a result, potentially harmful substances in urine are allowed to leak through the epithelium and penetrate the bladder muscle. Potassium, which occurs in high concentrations in normal urine, does not damage or penetrate a healthy urothelium but is highly toxic to tissues such as the bladder muscularis. The depolarization of sensory nerves in the bladder muscle by potassium could produce the symptoms of IC as well as cause its progression.

A growing body of data supports this hypothesis. On the basis of this model of IC pathogenesis, the Potassium Sensitivity Test (PST) was developed to test for the presence of abnormal bladder epithelial permeability. Although use of the PST is not yet generally accepted, a number of centers around the world have reported results of more than 2200 PSTs performed on IC patients [Parsons, et al. Urology 57:428-33 (2001), Parsons and Albo, J Urol 168:1054-1057 (2002); Koziol, Urol Clin North Am 21:7-71 (1994); Held, et al. in Interstitial Cystitis, Hanno, et al (Eds), Springer-Verlag, London, p: 29-48 (1990); Parsons, et al. Neurourol Urodyn 3:515-520 (1994); Payne and Browning, J Urol 155 (Suppl):438A (1996); Parsons, et al. J Urol 159:1862-1867 (1998); Chambers, et al. J Urol 162:699-701 (1999); Teichman and Nielson-Omeis, J Urol 161:1791-1794 (1999); Chen, et al. J Urol 165 (Suppl.):67 (2001); Daha, et al. J Urol 165 (Suppl):68 (2001); Forrest and Vo, Urology 57 (Suppl 6A):26-29 (2001); Kuo, Formos Med Assoc 100:309-314 (2001); Grégoire, et al. J Urol 168:556-557 (2002); Parsons, et al. Urology 59:329-333 (2002)]. The PST has been positive in 78% of those IC patients tested, providing considerable evidence most IC patients have a urothelial permeability defect, and that a positive PST is a valid indicator of the presence of IC [Parsons, et al. Urology 57:428-33 (2001); Parsons and Albo, J Urol 168: 1054-1057 (2002); Koziol, Urol Clin North Am 21:7-71 (1994); Held, et al. in Interstitial Cystitis, Hanno, et al (Eds), Springer-Verlag, London, p: 29-48 (1990); Parsons, et al. Neurourol Urodyn 3:515-520 (1994); Payne and Browning, J Urol 155 (Suppl):438A (1996); Parsons, et al. J Urol 159: 1862-1867 (1998); Chambers, et al. J Urol 162:699-701 (1999); Teichman and Nielson-Omeis, J Urol 161:1791-1794 (1999); Chen, et al. J Urol 165 (Suppl.):67 (2001); Daha, et al. J Urol 165 (Suppl):68 (2001); Forrest and Vo, Urology 57 (Suppl 6A):26-29 (2001); Kuo, Formos Med Assoc 100:309-314 (2001); Grégoire, et al. J Urol 168:556-557 (2002); Parsons, et al. Urology 59:329-333 (2002); Kuo, Urol Int 71:61-65 (2003)].

The epithelial permeability defect model of IC pathogenesis is the rationale for medical treatment of IC with heparinoid compounds, which are described in the next section. Investigators have documented increased mast cell activity and neurological upregulation in IC patients. Although the precise role of these processes in IC pathophysiology is not clear, both increased mast cell activity and neurological upregulation may contribute to the generation of IC symptoms in the lower urinary tract. Addressing the increased mast cell activity and neurological upregulation with oral hydroxyzine and amitriptyline, respectively, has proved to be helpful to many IC patients in our clinical practice.

IC is a relatively common disorder that may affect more than 7 million women in the United States as well as a surprising number of men. The gold standard for diagnosis of IC is clinical: the disease can be detected from the characteristic pattern of IC symptoms in the appropriate clinical setting and in the absence of other definable causes, which usually can be ruled out with urine analysis. Tools such as the PUF scale and the PST are useful in establishing the diagnosis of IC. The majority of patients with this condition can be treated successfully using a 3-part program to restore epithelial function, inhibit neural activation, and control allergies.

This treatment method addresses lower urinary epithelial dysfunction, a factor that appears to play a role in many cases of IC. As used herein, "lower urinary epithelial dysfunction" refers to disorders with positive potassium sensitivity tests (e.g. IC, prostatitis and the like). As used herein, "urinary dysfunction" refers to abnormal urination, patterns or bladder habits, including wetting, dribbling and other urination control problems. Using this treatment method, the clinician can provide both immediate and long-term control of symptoms while treating the underlying cause of the disease for the majority of IC patients.

The present invention focuses on treatment for the patients who make up the majority of the IC population, who have IC symptoms and are not currently receiving therapy for their disease. However it is not meant to limit the treatment to untreated IC patents nor to IC patients with typical symptoms and is meant to include those at either extreme who have mild symptoms and those with severe and debilitating IC, even though such cases of the latter are relatively rare. The present invention is not meant to limit the treatment to IC patients and is meant to include those patients with positive potassium sensitivity tests that would likely benefit from the treatment (e.g. prostatitis and the like).

Available Compounds

Heparinoid Compounds

For the majority of cases of IC, the cornerstone of treatment is heparinoid therapy. In some embodiments, compounds used for this purpose comprise intravesical heparin [Parsons, et al. Br J Urol 73:504-507 (1994); Ho, et al. Urology 53:1133-9 (1999)]. In some embodiments, compounds used for this purpose comprise oral pentosan polysulfate sodium (PPS) [Parsons, et al. J Urol 150:845-848 (1993); Mulholland, et al. Urology 35:552-558 (1990); Parsons, et al. J Urol 138:513-516 (1987); Holm-Bentzen, et al. J Urol 138:503-507 (1987); Hanno, Urology 49 (Suppl 5A):93-99 (1997); Nickel, et al. J Urol 165 (5 Suppl):67 (2001)].

Oral Pentosan Polysulfate Sodium (PPS)

Pentosan polysulfate sodium (PPS), whose structure is similar to that of the GAGs in the lower urinary tract, appears to allow the restoration of the urothelial mucus layer [Parsons, et al. Urology 59:329-333 (2002); Parsons, Urology 49 (Suppl. 5A):100-104 (1997)]. PPS is the only FDA-approved oral medication for treating IC in the United States (e.g. Pentosan polysulfate sodium (ELMIRON)). It is currently the most effective IC treatment available [Hanno, Urology 49 (Suppl 5A):93-99 (1997); Nickel, et al. J Urol 165 (5 Suppl): 67 (2001)], as well as the most rigorously tested in clinical trials. Data from longitudinal studies in open phase have shown that the rate of response to PPS increases with the duration of treatment, reaching approximately 70% after 8-12 months of therapy [Hanno, Urology 49 (Suppl 5A):93-99 (1997); Nickel, et al. J Urol 165 (5 Suppl):67 (2001)].

Intravesical Heparin

Particularly in severe IC, intravesical heparin can be used either alone or in combination with PPS [Parsons, et al. Br J Urol 73:504-507 (1994); Ho, et al. Urology 53:1133-9 (1999)]. For chronic therapy, intravesical heparin can be prescribed at a dose of 10,000-40,000 IU in 10 ml water daily. For maintenance, this same heparin and water solution can be instilled three times weekly, typically on a Monday-Wednesday-Friday schedule [Parsons, et al. Br. J. Urol 73:504-507 (1994)]. For immediate relief of IC pain and urgency, heparin can also be used in place of PPS in one embodiment for an intravesical therapeutic solution, which is described below.

Intravesical instillations of hyaluronic acid, a glycosaminoglycan marketed in Canada as Cystistat, may be of benefit for some IC patients. Clinical trials of hyaluronic acid are underway in the United States, but this compound is not approved for U.S. use.

The present invention contemplates the substitution of hyaluronic acid for heparin (described below).

EXAMPLE 2

Current Practice

Most patients who have IC/LUDE will benefit from multimodal medical treatment based on heparinoid therapy. As an adjunct to this regimen, a program of intravesical therapy can be beneficial in providing immediate, temporary symptom relief to patients whose disease is more severe or long standing. The multimodal oral treatment regimen for IC has three parts (FIG. 6): heparinoid therapy to restore lower urinary tract epithelial function, tricyclic antidepressant therapy to inhibit neural activation, antihistamine therapy to control any allergies.

Once other causes have been ruled out, a patient who has signs and symptoms of IC should be started on the treatment regimen described here. If it is the physician's clinical impression that the patient has IC, IC treatment should not be withheld on the basis of a negative PST and/or negative findings on cystoscopy.

Restoring Lower Urinary Tract Epithelial Function

In some embodiments, PPS is given at 300 mg/day in two or three divided doses. In some embodiments, a higher dose is used. For example, PPS is given at 600 mg/day in two or three divided doses for male IC patients.

In some embodiments, intravesical therapy is used either alone or in combination with PPS. A patient who has severe IC can supplement an oral PPS regimen with intravesical therapy instillations performed daily or twice daily. The recommended solution contains heparin 40,000 IU in 10 mL 1% lidocaine (w/v) (or 16 mL 2% lidocaine if 1% is not effective) and 3 ml of sodium bicarbonate (see below). The sodium bicarbonate promotes absorption of the lidocaine [Henry, et al. J Urol 165:1900-1903 (2001)]. In most cases, the intravesical therapy can be tapered slowly and then discontinued as the patient's symptoms improve. As used herein, "anesthetic" refers to a class of medication that blocks the sensation of pain. As used herein, "local anesthetic" refers to a class of medication that temporarily stops the sensation of pain in a particular area of the body. It is not meant to limit the specific local anesthetic and can include one or more of the following: benzocaine, lidocaine, tetracaine, bupivacaine, cocaine, etidocaine, flecainide, mepivacaine, pramoxine, prilocalne, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Preferably, the local anesthetic is selected from the group consisting of lidocaine, bupivicaine, benzocaine, tetracaine, etidocaine, flecainide, prilocalne, and dibucaine. Generic formulations of these compounds, mixtures containing these compounds, salt formulations of these compounds and the like. In some embodiments, a local anesthetic is a lidocaine (e.g. Example 2 and 3). Local anesthetics include mixtures of local anesthetics (e.g. lidocaine and prilocalne).

Because it may take time for upregulated nerves in the lower urinary tract to deactivate, an IC patient's symptoms of urgency and pain can persist after heparinoid therapy has restored the urothelium. For these reasons, the clinician should assess the results of heparinoid therapy only after at least a year of treatment in cases of mild to moderate disease, and only after at least two years of treatment in a case of severe IC. In general, if a patient does not appear to be responding to heparinoid therapy, adding other treatments to the regimen rather than discontinuing the heparinoid therapy is recommended.

Intravesical Treatment for Immediate Relief of Symptoms

Data from preliminary studies for one embodiment of an intravesical therapeutic solution can provide immediate temporary relief of the symptoms of urgency and pain in IC patients [Dell and Parsons, Abstract presented at NIDDK/Interstitial Cystitis Association Symposium, Research Insights into Interstitial Cystitis, Alexandria, Va., (Oct. 30-Nov. 1, 2003); Davis, et al. Abstract presented at NIDDK/Interstitial Cystitis Association Symposium, Research Insights into Interstitial Cystitis, Alexandria, Va. (Oct. 30-Nov. 1, 2003); Parsons, Contemp Urol 15: 22-24, 27-28, 31-32, 35 (2003)]. One of the methods of the present invention combines heparin and lidocaine buffered with sodium bicarbonate to pH >8.0 via direct catheter delivery to the bladder, providing immediate and long term pain relief for chronic IC sufferers. In some embodiments, the solution contains 10,000-40,000 units of heparin. In some embodiments, heparin is replaced by 100-200 mg PPS (the contents of an oral capsule dissolved in 10 mL buffered normal saline), 10 mL 1% lidocaine or 16 mL 2% lidocaine, and 3 mL 8.4% sodium bicarbonate (w/v). The solution is instilled into the empty bladder and retained for approximately 30 minutes. The principal difference between this therapeutic solution and other such solutions is the presence of sodium bicarbonate, which dramatically increases the absorption of the lidocaine. In one preliminary study using PPS, 41 of 55 patients (75%) experienced significant immediate relief of their IC symptoms. Use of the solution 3-7 times weekly for two weeks or more resulted in sustained pain relief in 85% of patients [Parsons and Davis, Practice Building Today Sep.: 18-22 (2003)].

EXAMPLE 3

At the start of the study, each patient underwent intravesical instillation of a therapeutic solution composed of 40,000 U heparin, 8 mL of 1% lidocaine (80 mg; group 1), and 3 mL of 8.4% sodium bicarbonate suspended in a volume of 15 mL total fluid. After 47 patients had been treated with one instillation of this solution, and no adverse events or side effects had developed, it was decided to increase the amount of lidocaine in the solution. Subsequently, all subjects received this modified solution, which was identical to the original solution, except that it contained 8 mL of 2% lidocaine (160 mg; group 2). All patients were evaluated for pain and urgency relief within 20 minutes of the single instillation. Group 2 patients were evaluated by telephone follow-up 24 to 48 hours after the instillation to determine the duration of their relief. In addition, group 2 patients who elected to receive additional instillations of the 2% lidocaine solution were evaluated to determine whether the efficacy of the solution persisted after a course of three treatments per week for 2 weeks. All patients were evaluated using the Patient Overall Rating of Improvement of Symptoms scale (FIG. 9) on which they rated their symptoms of pain and urgency as "worse" or from "no better" (0% improvement) to "symptoms gone" (100% improvement) in 25% increments. Significant symptom relief was defined as a 50% or greater improvement in symptoms.

Figure 10:
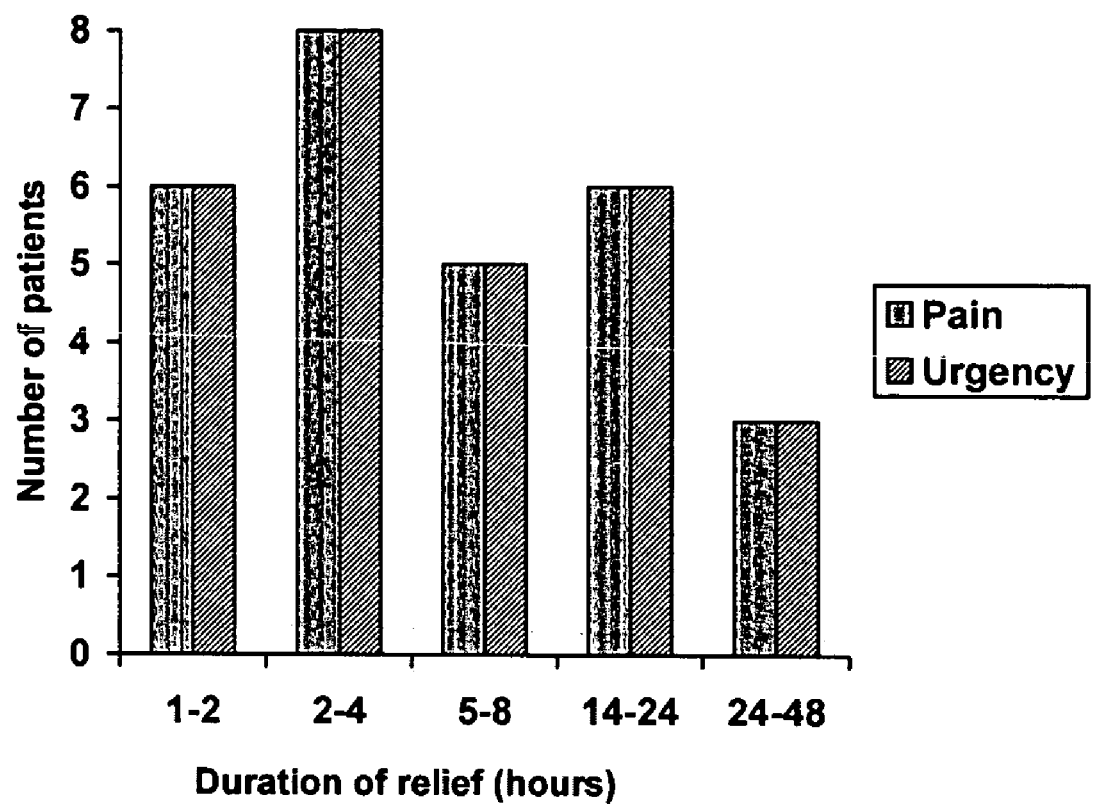
FIG. 10 shows the duration of relief of pain and urgency in 28 patients with IC who received one intravesical instillation of therapeutic solution containing 160 mg lidocaine.

A total of 82 subjects were evaluated, 47 in group 1 and 35 in group 2. The mean patient age was 35 years (range 22 to 65). After one instillation, significant immediate relief of both pain and urgency was obtained in 35 (75%) of 47 subjects who received the 1% lidocaine/heparin/sodium bicarbonate solution (group 1) and in 33 (94%) of 35 who received the 2% lidocaine/heparin/sodium bicarbonate solution (group 2). The difference in the response rates between groups 1 and 2 was statistically significant (P<0.01; chi-square analysis). Twenty-eight patients in group 2 were available for the evaluation of the duration of relief by telephone follow-up 24 to 48 hours after the single instillation. One half of these patients experienced at least 4 hours of symptom relief from the instillation (FIG. 10). Twenty patients in group 2 agreed to receive a course of three instillations per week for 2 weeks. Of the 20 patients, 16 (80%) reported significant sustained relief of pain and urgency. In all subjects, the symptom relief lasted for at least 48 hours after the last intravesical treatment.

In addition to the safety and efficacy indicated by the preliminary data, the intravesical therapeutic solution has several advantages. Patients can be taught to self-administer the instillations at home. Heparin and PPS appear to have equal efficacy in the therapeutic solution; PPS offers the advantage of significantly lower cost. In addition, the solution can provide a therapeutic option for patients who are unable to take the oral form of PPS.

Other Adjunct Therapies

In cases of severe IC or disease that is refractory to more conservative management, patients may benefit from the use of implantable neurostimulators. Referral to a pain clinic for chronic pain management may also be helpful.

Other Factors

In a small percentage of cases, a factor that can affect the choice of therapy within the multimodal IC treatment regimen is the patient's ability to tolerate oral PPS. If a patient receiving oral PPS has signs of gastrointestinal distress, or if the patient feels otherwise unable to take the oral PPS, the PPS can be administered via the intravesical therapeutic solution described above. This alternative bypasses the oral route of administration and the accompanying potential for drug side effects. It is also less expensive than oral PPS treatment.

CONCLUSIONS

IC is a relatively common disorder that may affect as many as 1 in 4.5 women [Parsons, et al. Urology 60:573-578 (2002)] and 1 in 20 men [Nickel, et al. J Urol 165:842-845 (2001)]. The disease can readily be detected from the characteristic pattern of its symptoms in the appropriate clinical setting and in the absence of other definable causes. In establishing the diagnosis, tools such as the PUF Scale and the PST are useful. The majority of cases of IC can be treated successfully using a multimodal program of therapy directed at restoring lower urinary epithelial function, reversing neural activation, and controlling any allergies. In severe or long-standing cases of IC, an intravesical treatment program can be an important adjunct that provides both immediate and long-term symptom relief (Table 5 and 6, i.e. FIGS. 7 and 8, respectively).

What is claimed is:

1. A method for inhibiting Interstitial Cystitis and its symptoms in a subject in need thereof, said method comprising administering to said subject an effective amount of a composition comprising a heparinoid, a local anesthetic agent and a buffering compound, thereby inhibiting Interstitial Cystitis and its symptoms in the subject.

2. The method of claim 1 further comprising administering to said subject an effective amount of an osmolar component.

3. The method of claim 2, wherein the composition is in solution and the osmolar component is present in a sufficient amount so that the final solution is isotonic or near isotonic.

4. The method of claim 3, wherein the osmolar component is at least one of sodium chloride, dextrose, dextran 40, dextran 60, starch and mannitol or a combination thereof.

5. The method of claim 1, wherein the local anesthetic agent is at least one of lidocaine, bupivacaine, and mepivacaine.

6. The method of claim 1, wherein the heparinoid comprises at least one of a heparin, a pentosan polysulfate sodium, a heparan sulfate, a heparin sodium, a hyaluronic acid, and a chondroitin sulfate.

7. The method of claim 6, wherein the heparinoid comprises at least one of a heparin, a heparan sulfate, a heparin sodium, a hyaluronic acid, and a chondroitin sulfate, and the method further comprises the administration to said subject of an effective amount of sodium pentosan polysulfate to inhibit Interstitial Cystitis.

8. The method of claim 7, wherein the sodium pentosan polysulfate is administered orally.

9. The method of claim 8, wherein the sodium pentosan polysulfate is in a quantity from about 100 mg/day to about 600 mg/day.

10. The method of claim 9, wherein the sodium pentosan polysulfate is in a quantity from about 100 mg/day to about 300 mg/day.

11. A method for repairing a mucin layer of bladder tissue by the method of claim 1 thereby inhibiting Interstitial Cystitis.

12. The method of claim 1, wherein the buffering compound comprises at least one of sodium bicarbonate and THAM (tromethamine or Tris hydroxymethylpropyl).

13. The method of claim 1, wherein the effective amount of the buffering compound is 3 ml of 8.4% sodium bicarbonate (w/v) per unit dose.

14. The method of claim 1, wherein the effective amount of the heparinoid is
  (i) about 0.5 mg to about 1000 mg of heparin per unit dose;
  (ii) about 1 mg to about 600 mg of pentosan polysulfate sodium per unit dose;
  (iii) about 0.5 mg to about 10,000 mg of heparan sulfate per unit dose;
  (iv) about 5 mg to about 600 mg of hyaluronic acid per unit dose;
  (v) about 1 mg to about 10,000 mg of chondroitin sulfate per unit dose; or
  (vi) about 10 mg to about 600 mg of heparin sodium per unit dose.

15. The method of claim 1, wherein the effective amount of the anesthetic agent is 10 ml of 1% lidocaine or 16 ml of 2% lidocaine per unit dose.

16. The method of claim 1, wherein the heparinoid, the anesthetic agent, and the buffering compound are administered concomitantly or in sequence.

17. The method of claim 2, wherein the heparinoid, the anesthetic agent, the buffering compound and the osmolar component are administered concomitantly or in sequence.

18. The method of claim 1, wherein the subject is selected from the group consisting of human, monkey, ape, dog, cat, cow, horse, rabbit, mouse and rat subjects.

19. The method of claim 1, wherein administration to said subject is effected by intravesicular administration, administration using liposomes, administration using biodegradable polymers, or administration using a hydrogel.

20. The method of claim 2, wherein the heparinoid, the anesthetic agent, the buffering compound and the osmolar component are in solution.

21. The method of claim 20, wherein the solution has a pH from about 7 to 12.

22. A method for monitoring the course of Interstitial Cystitis in a subject, said method comprising
   intravesicularly administering a solution containing an amount of potassium that would elicit pain in a subject that has a compromised urothelium, wherein the subject has been administered the composition, comprising a heparinoid, a local anesthetic agent, and a buffering compound, and
   monitoring the pain response of the subject at different points in time,
   whereby a difference in the amount of pain determined is indicative of the course of the Interstitial Cystitis condition.

* * * * *